United States Patent
Quick et al.

(10) Patent No.: US 10,626,358 B2
(45) Date of Patent: Apr. 21, 2020

(54) SYSTEMS AND METHODS FOR TISSUE PROCESSING AND PREPARATION OF CELL SUSPENSION THEREFROM

(71) Applicant: Avita Medical Ltd, Valencia, CA (US)

(72) Inventors: Andrew Perry Quick, Valencia, CA (US); David Allen Fencil, Valencia, CA (US); William Ford Dolphin, Topanga, CA (US)

(73) Assignee: AVITA MEDICAL LTD, Valencia, CA (US)

(*) Notice: Subject to any disclaimer, the term of this patent is extended or adjusted under 35 U.S.C. 154(b) by 163 days.

(21) Appl. No.: 14/776,038

(22) PCT Filed: Mar. 14, 2014

(86) PCT No.: PCT/US2014/028944
§ 371 (c)(1),
(2) Date: Sep. 14, 2015

(87) PCT Pub. No.: WO2014/153072
PCT Pub. Date: Sep. 25, 2014

(65) Prior Publication Data
US 2016/0024450 A1    Jan. 28, 2016

Related U.S. Application Data

(60) Provisional application No. 61/783,422, filed on Mar. 14, 2013.

(30) Foreign Application Priority Data

Apr. 13, 2013    (AU) .................................. 2013205148

(51) Int. Cl.
*C12M 3/00* (2006.01)
*C12M 1/33* (2006.01)

(52) U.S. Cl.
CPC ............ *C12M 21/08* (2013.01); *C12M 45/02* (2013.01)

(58) Field of Classification Search
CPC ...... C12M 21/08; C12M 45/02; C12M 45/06; C12M 47/04; C12M 45/00; C12M 29/04;
(Continued)

(56) References Cited

U.S. PATENT DOCUMENTS 1,356,794 A    10/1920   Smith
3,608,553 A    9/1971   Balamuth
(Continued)

FOREIGN PATENT DOCUMENTS

AU      P02752     10/1996
AU      3990197     4/1998
(Continued)

OTHER PUBLICATIONS

PCT International Search Report issued in International Application No. PCT/US 2014/028944 dated Aug. 1, 2014.
(Continued)

*Primary Examiner* — William H. Beisner
*Assistant Examiner* — Danielle B Henkel
(74) *Attorney, Agent, or Firm* — Cooley LLP

(57) ABSTRACT

The present invention provides for methods and at least partially automated devices suitable for producing a transplantable cellular suspension of living tissue suitable for promoting tissue regeneration in an epithelium-related procedure, as well as compositions produced therefrom. Tissue regeneration in humans is extremely limited and constitutes a major challenge to the repair of damaged organ function. Wound treatment is a typical area where tissue regeneration is required. Wounds (lacerations or openings) in mammalian tissue can result in tissue disruption and coagulation of the microvasculature at the wound face.

25 Claims, 19 Drawing Sheets

(58) Field of Classification Search
CPC .......... A61B 17/00; A61M 1/00; A61K 35/28; C12N 5/0667
See application file for complete search history.

(56) References Cited

U.S. PATENT DOCUMENTS

| | | | |
|---|---|---|---|
| 3,647,632 | A | 3/1972 | Johnson et al. |
| 3,860,706 | A | 1/1975 | Ikeda et al. |
| 4,059,486 | A | 11/1977 | Tolbert |
| 4,254,226 | A | 3/1981 | Eisinger et al. |
| 4,304,866 | A | 12/1981 | Green et al. |
| 4,350,768 | A | 9/1982 | Tihon et al. |
| 4,377,010 | A | 3/1983 | Fydelor et al. |
| 4,418,691 | A | 12/1983 | Yannas et al. |
| 4,458,678 | A | 7/1984 | Yannas et al. |
| 4,510,144 | A | 4/1985 | Hadden et al. |
| 4,533,635 | A | 8/1985 | Guedon born Saglier et al. |
| 4,649,115 | A | 3/1987 | Safai et al. |
| 4,769,317 | A | 9/1988 | Hefton |
| 5,000,963 | A | 3/1991 | Hefton |
| 5,035,708 | A | 7/1991 | Alchas et al. |
| 5,079,160 | A | 1/1992 | Lacy et al. |
| 5,145,770 | A | 9/1992 | Tubo et al. |
| 5,292,655 | A | 3/1994 | Wille, Jr. |
| 5,328,695 | A | 7/1994 | Lucas et al. |
| 5,334,527 | A | 8/1994 | Brysk |
| 5,352,668 | A | 10/1994 | Burgeson et al. |
| 5,352,806 | A | 10/1994 | Gunawardana et al. |
| 5,441,539 | A | 8/1995 | Alchas et al. |
| 5,460,939 | A | 10/1995 | Hansbrough et al. |
| 5,507,385 | A | 4/1996 | Koloski et al. |
| 5,556,783 | A | 9/1996 | Lavker et al. |
| 5,601,728 | A | 2/1997 | Kayal et al. |
| 5,624,638 | A | 4/1997 | Negrotti |
| 5,786,207 | A | 7/1998 | Katz et al. |
| 5,814,511 | A | 9/1998 | Chang et al. |
| 5,866,167 | A | 2/1999 | Van Bossuyt |
| 5,955,343 | A | 9/1999 | Holmes et al. |
| 5,994,129 | A | 11/1999 | Armstrong et al. |
| 6,080,581 | A | 6/2000 | Anderson et al. |
| 6,207,451 | B1 | 3/2001 | Dennis et al. |
| 6,432,666 | B1 | 8/2002 | Hart |
| 7,655,465 | B2 | 2/2010 | Sherley et al. |
| 7,850,983 | B2 | 12/2010 | Sevrain et al. |
| 8,022,037 | B2 | 9/2011 | Li et al. |
| 8,580,564 | B2 | 11/2013 | Brown et al. |
| 8,893,995 | B2* | 11/2014 | Taghizadeh ............ C12M 45/02 241/69 |
| 9,029,140 | B2 | 5/2015 | Wood et al. |
| 9,057,064 | B1* | 6/2015 | Dyer .................... C12N 15/101 |
| 9,078,741 | B2 | 7/2015 | Wood et al. |
| 9,150,826 | B2* | 10/2015 | Isely .................... C12N 1/066 |
| 9,867,692 | B2 | 1/2018 | Wood et al. |
| 2001/0048917 | A1 | 12/2001 | Hoeffler et al. |
| 2002/0019060 | A1* | 2/2002 | Petersen ................ B01L 3/502 436/514 |
| 2002/0048563 | A1 | 4/2002 | Baetge et al. |
| 2002/0106353 | A1 | 8/2002 | Wood et al. |
| 2005/0026275 | A1 | 2/2005 | Bahoric |
| 2005/0255096 | A1 | 11/2005 | Poder |
| 2005/0260175 | A1* | 11/2005 | Hedrick ................ A61B 17/00 424/93.7 |
| 2005/0272147 | A1 | 12/2005 | Sherley et al. |
| 2007/0069054 | A1 | 3/2007 | Shomi |
| 2007/0184033 | A1 | 8/2007 | Sevrain et al. |
| 2007/0286880 | A1 | 12/2007 | Vasiliev et al. |
| 2008/0014181 | A1 | 1/2008 | Ariff et al. |
| 2010/0035815 | A1 | 2/2010 | Li et al. |
| 2010/0159507 | A1* | 6/2010 | Ting ....................... C12M 35/04 435/40.5 |
| 2010/0196334 | A1 | 8/2010 | Wood et al. |
| 2010/0255052 | A1 | 10/2010 | Young Anze et al. |
| 2010/0279405 | A1 | 11/2010 | Peterson et al. |
| 2010/0285588 | A1 | 11/2010 | Stubbers et al. |
| 2011/0070646 | A1 | 3/2011 | Brown et al. |
| 2011/0082082 | A1 | 4/2011 | Li et al. |
| 2011/0150848 | A1 | 6/2011 | Wood et al. |
| 2011/0318315 | A1 | 12/2011 | Aggarwal et al. |
| 2012/0043405 | A1 | 2/2012 | Faulker et al. |
| 2012/0264689 | A1 | 10/2012 | Mize |
| 2015/0079153 | A1 | 3/2015 | Quick et al. |
| 2015/0104825 | A1* | 4/2015 | Peyvan .................. G01N 1/286 435/30 |
| 2015/0182739 | A1 | 7/2015 | Wood et al. |
| 2018/0098840 | A1 | 4/2018 | Wood et al. |

FOREIGN PATENT DOCUMENTS

| | | |
|---|---|---|
| CN | 1625398 A | 6/2005 |
| CN | 1878470 A | 12/2006 |
| CN | 101500512 A | 8/2009 |
| CN | 102089425 A | 6/2011 |
| EP | 0 350 887 A2 | 1/1990 |
| EP | 0 444 270 A1 | 9/1991 |
| EP | 0 751 217 A1 | 5/1999 |
| EP | 2502986 | 9/2012 |
| EP | 2828378 | 1/2015 |
| JP | S-58-501817 A | 10/1983 |
| JP | 04-218147 A | 8/1992 |
| JP | 2002-537851 A | 12/2002 |
| JP | 2004-529872 A | 9/2004 |
| JP | 2008-504816 A | 2/2008 |
| JP | 2010-524498 A | 7/2010 |
| WO | WO-83/01384 A1 | 4/1983 |
| WO | WO-90/00739 A1 | 1/1990 |
| WO | WO-97/23602 A1 | 7/1997 |
| WO | WO-98/53850 A2 | 12/1998 |
| WO | WO-98/53850 A3 | 12/1998 |
| WO | WO-98/56897 A1 | 12/1998 |
| WO | WO-99/12555 A1 | 3/1999 |
| WO | WO-99/21963 A1 | 5/1999 |
| WO | WO-00/32207 A1 | 6/2000 |
| WO | WO-00/53797 A1 | 9/2000 |
| WO | 2002/062358 | 8/2002 |
| WO | 2002/066598 | 8/2002 |
| WO | WO-03/063870 A1 | 8/2003 |
| WO | 2005/034843 | 4/2005 |
| WO | 06014159 | 2/2006 |
| WO | WO-2006/014156 A1 | 2/2006 |
| WO | WO-2007/092801 A2 | 8/2007 |
| WO | WO-2007/092801 A3 | 8/2007 |
| WO | WO-2008/133874 A1 | 11/2008 |
| WO | WO-2009/136173 A2 | 11/2009 |
| WO | WO-2009/136173 A3 | 11/2009 |
| WO | 2013019154 | 2/2013 |
| WO | 2013/030761 | 3/2013 |
| WO | 2013/142254 | 9/2013 |
| WO | WO-2014/153072 A1 | 9/2014 |

OTHER PUBLICATIONS

Extended European Search Report issued in European application No. 14770177.5 dated Sep. 26, 2016.
Adams, B.F. et al. (2000). "The role of respiratory epithelium in a rat model of obliterative airway disease," Transplantation 69: 661-693.
Anonymous, "Recell patient leaflet," Absolute Makeover, Apr. 21, 2011, http://www.absolutemakeover.com.au/_literature_46887/Recell_Patient_Leaflet.
Anonymous: "Clinical Cell Culture-Recell®" Internet Article, Online, Dec. 17, 2003.
Anonymous "Understanding mesh sizes," http://www.espimetals.com/index.php/online-catalog/334-understanding-mesh-sizes.
Antoni et al, "Development of the Total Care Unit." ANZBA (Queenstown) (1997) (Abstract).
Atala, A. et al. (1992). "Formation of urothelial structures in vivo from dissociated cells attached to biodegradable polymer scaffolds in vitro," J Urol 148: 658-662.
Backman et al, "Scientific Visualisation as an Aide to Quantifying the Extent of Burn Injury." ANZBA (Gold Coast) (1995) (Abstract).

(56) References Cited

OTHER PUBLICATIONS

Barnden and Wood, "Adult Burn Patients Treated with a Combination of Skin Graft Techniques—What Dressing System to Use?" ANZBA (Gold Coast) (1995) (Abstract).
Barnden and Wood, "Designing a Tool to Facilitate and Standardise Burn Care in W. A." ANZBA (1996) (Abstract).
Barnden and Wood, "Dressings Used in the Burn Treated with Cultural Epidermal Autograft" ANZBA (Canberra) (1993) (Abstract).
Barrera, "The Use of Micrografts and Minigrafts for the Treatment of Burn Alopecia" Plast. and Reconstr. Surg. 103(2):581-584 (Feb. 1999).
Ben-Porath et al.; "When cells get stressed: and integrative view of cellular senescence"; The Journal of Clinical Investigation; vol. 113; No. 1; pp. 8-13; Jan. 2004.
Bird and Wood, "New Techniques of Managing Palmer Burns" ANZBA (May 1994) (Abstract).
Blennerhasset and Wood, "The Use of the Ultrasonic Aspiration as a Tissue Dissector for Excision of Burn Escar" ANZBA p. 40 (1996) (Abstract).
Booth and Wood, "Scar Assessment for the Future" ANZBA (Canberra) (1993) (Abstract).
Boyce, S.T., Ham, KG., "Cultivation, frozen storage and clonal growth of normal human epithelial keratinocytes in serum-free media." J. Tissue Cult. Methods 9:83-93 (1985).
Brandy, "A New Instrument for the Expedient Production of Minigrafts" J. Dermatol. Surg. Oncol. 18:487-492 (1992).
Burgeson RE et al. 1997. The dermal-epidermal junction. Curr Op Cell Biol 9: 651-658.
Caldow and Wood, "The Use of Self Adhesive Elastic Bandaging to Control Oedema in the Burn Injured Hand" ANZBA (Gold Coast) p. 35 (1995) (Abstract).
Cena et al, "Computerised Intergration of Multimodality Imaging in Scar Assessment." ANZBA (Gold Coast) p. 20 (1995) (Abstract).
Cheng, Chieh-Fang et al., "A fragment of secreted Hsp90a carries properties that enable it to accelerate effectively both acute and diabetic wound healing in mice." The Journal of Clinical Investigation; vol. 121, No. 11; pp. 4348-4361; Nov. 2011.
Compton, "Wound Healing Potential of Cultured Epithelium" Wounds 5(2):97-111 (Mar./Apr. 1993).
Cooper et al., "The Effect of Aprotinin on Human Cultured Epidermal Cells" PAN/Asian European Tissue Repair Society Wound Healing Meeting (1997) (Abstract).
DeJong et al., "Pathways in Therapy for Burns Patients" ANZBA (Queenstown) (1997) (Abstract).
Deluca, M., et al., "Human Epithelial Cells Induce Human Melanocyte Growth In Vitro but Only Skin Keratinocytes Regulate Its Proper Differentiation in the Absence of Dermis," The Journal of Cell Biology, 107:1919-1926, (Nov. 1988).
Devalia et al., "Culture and comparison of human bronchial and nasal epithelial cells in vitro" Resp. Med. 84:303-312 (1990).
Ding and Han, "Recent Advances in Burn Wound Management in China" Acta Chirurgiae Plasticae 31(2):84-91 (1989).
Dzubow, "Scar Revision by Punch-Graft Transplants" J. Dermatol. Surg. Oncol. 11(12): 1200-1202 (Dec. 1985).
Early Burn Management Report. PNAZBA (1997) (Abstract).
Edgar and Wood, "Silicone Oil Revisited" ANZBA (Manly) P0-18:49 (1998) (Abstract).
Edgar et al., "Playing in a Team can be a Pain" ANZBA (Tasmania) p. 65 (1999) (Abstract).
Edgar et al., "The Good Oil?" ANZBA (Tasmania) p. 37 (1999) (Abstract).
Education—The Key to Better Management of the Burn Victim: An education project in Western Australia. Presentation. Rural National Health Meeting (1995) (Abstract).
Eisinger, M. et al. (1979). "Human epidermal cell cultures: Growth and differentiation in the absence of dermal components or medium supplements," PNAS 76:5340-5344.
Elliget and Lechner, "Human Bronchial Epithelial Cell Culture. Specialized Vertebrate Cultures" Respir. Sys. Module I3B3: 1-17 (Abstract).

Extended European Search Report dated Feb. 27, 2004, for EP Application No. 02 709 917.5, 6 pages.
Extended European Search Report dated Dec. 8, 2011, for EP Application No. 10 184 235.9, 12 pages.
Extended European Search Report dated Sep. 18, 2015, for EP Application No. 15 159 890.1, 9 pages.
Extended European Search Report dated Oct. 2, 2015, for EP Application No. 13 764 726.9, filed on Mar. 14, 2013, 7 pages.
Extended European Search Report dated Sep. 26, 2016, for EP Application No. 14 770 177.5, filed on Mar. 14, 2014, 15 pages.
Falabella et al., "Surgical Combination Therapy for Vitiligo and Piebaldism" Dermatol. Surg. 21 :852-857 (1995).
Falabella, "Repigmentation of Leukoderma by Minigrafts of Normally Pigmented, Autologous Skin" J. Dermatol. Sur. Oncol. 4:916-919 (Dec. 1978).
Final Office Action in U.S. Appl. No. 10/068,299 dated Jul. 13, 2007.
Final Office Action in U.S. Appl. No. 10/068,299 dated Sep. 23, 2008.
Final Office Action in U.S. Appl. No. 10/068,299 dated Jul. 9, 2010.
Final Office Action in U.S. Appl. No. 13/223,577 dated Oct. 22, 2012.
Final Office Action in U.S. Appl. No. 13/223,577 dated Sep. 24, 2014.
Final Office Action in U.S. Appl. No. 13/036,569 dated Mar. 9, 2012.
Final Office Action in U.S. Appl. No. 13/036,569 dated Oct. 10, 2013.
Final Office Action in U.S. Appl. No. 12/699,554 dated Dec. 31, 2012.
Zhang et al., "Microskin grafting. IL Clinical report" Burns 12(8):544-548 (1986).
Final Office Action dated Feb. 25, 2019, for U.S. Appl. No. 15/838,429, filed Dec. 12, 2017, 19 pages.
Fong et al., "The Use of Clinical Indicators to Measure a Minimum Standard of Care for Early Burn Management" ANZBA (Queenstown) (1997).
Franklin et al., "Expansion of Bronchial Epithelial Cell Populations by In Vitro Culture of Explants from Dysplastic and Histologically Normal Sites" Am. J. Respir Cell. Mal. Biol. 15:297-304 (1996).
Fraulin, F.O.G. et al. (1998). "Autotransplantation of epithelial cells in the pig via an aerosol vehicle," J Burn Care Rehabil 19:337-345.
Fulda, et al. "Cellular Stress Responses: Cell Survival and Cell Death." International Journal of Cell Biology; vol. 2010; Article ID 214074; pp. 1-23 (2010).
Gallico, III, M.D., et al., "Permanent Coverage of large Burn Wounds with Autologous Cultured Human Epithelium", The New England Journal of Medicine, vol. 31, No. 7, pp. 448-451, Aug. 16, 1984.
Gauthier and Surleve-Bazeille, "Autologous grafting with noncultured melanocytes: A simplified method for treatment of depigmented lesions" J. Am. Acad. Dermatol. 26(1:1):191-194 (1992).
Giele et al., "An alternative technique for the harvesting of cultured epithelial cell sheets" Meth. Cell Sci. 17:233-236 (1995).
Giele et al., "Anatomical Variations in Pressures Generated by Pressure Garments" Plast. Reconstruct. Surg. 101(2):399-406 (Feb. 1998).
Giele et al., "Direct measurement of cutaneous pressures generated by pressure garments" Burns 23(2):137-141 (1997).
Giele et al., "Early Use of Pressure Masks to Avoid Facial Contracture During the Pregrafting Phase" J. Burn Care Rehabil. 16:641-645 (1995).
Giele et al., "Management of full thickness burns to lactating breasts" Burns 20(3):278-280 (1994).
Gospodarowicz and Greenburg, "The Role of Growth Factors and Extracellular Matrices in the Control of Mammalian Cell Proliferation" The Biology of Normal Human Growth (M. Ritzen et al., ed) Raven Press pp. 1-19 (1991).
Goulet et al., "Morphologic and Functional Properties of Bronchial Cells Isolated from Normal and Asthmatic Subjects" Am. J. Respir. Cell. Mal. Biol. 15:312-318 (1996).

(56) References Cited

OTHER PUBLICATIONS

Gramlich, G., "ReCell ein Erfahrungsbericht," Internet article, Online, Apr. 21, 2011, http://www.hagenmuehle.de/documents/MicrosoftWord-RecellVeroffentlichunginternet_000.pdf.
Griffiths and Wood, "The Influence of Geography on Burn Outcome" ANZBA (1994) (Abstract).
Griffiths and Wood, "The Use of Epidermal Derived Factors to Influence Wound Healing" ANZBA (Gold Coast) p. 11 (1995) (Abstract).
Griffiths et al., "Itch" ANZBA (Queenstown) (1997) (Abstract).
Guedon et al: "Culture and cytogenetic studies of adult human keratinocytes using a new growth factor", Differentiation, vol. 19, No. 2,1981 (109-114).
Habberfield and Wood, "Burn Unit Support Groups—A Burning Issue" ANZBA (Canberra) p. 46 (1993) (Abstract).
Haberfeld and Wood, "Psychological Aspects of Burn Injury: Research Issues" ANZBA (Gold Coast) p. 67 (1995) (Abstract).
Haberfeld et al., "Psychological Reactions to Trauma: A Survey of Burns Unit Staff" ANZBA p. 42 (1996) (Abstract).
Hentzer and Kobayasi, "Suction Blister Transplantation for Leg Ulcers" Acta Dermatovener (Stockholm) 55:207-209 (1975).
Hicks, W. et al. (1997). "Isolation and characterization of basal cells from human upper respiratory epithelium," Exp Cell Res 237:357-363.
Hirobe T. 1991, "Selective growth and serial passage of mouse melanocytes from neonatal epidermis in a medium supplemented with bovine pituitary extract," J Exp. Zool 257:184-194.
Hirobe: "Melanocyte stimulating hormone induces the differentiation of mouse epidermal melanocytes in serum-free culture", J. Cell. Phys., vol. 152, No. 2, Aug. 1992 (337-345).
Hornum and Wood, "Tragic Tales—Paediatric Burns in Motor Vehicles" ANZBA (1996) (Abstract).
Hornum and Wood, "Use of Retention Dressings in the Paediatric Population for Partial Thickness Burn Injury" ANZBA (May 1994) (Abstract).
Hornum et al., "The Impact of Integra™ Dermal Template Reconstruction on Paediatric Burn Care" ANZBA p. 82 (1999) (Abstract).
Hornum et al., "The Post Operative Management of Paediatric Burns Patients Treated with Cultured Epithelial Autograft in Fluid Suspension" ANZBA (Gold Coast) p. 18 (1995) (Abstract).
Humphrey, "Burns Education in Intensive Care" ANZBA P0-19:49 (1998) (Abstract).
Hunyadi, J. et al. (1987). "Keratinocyte grafting: Covering of skin defects by separated autologous keratinocytes in a fibrin net," Journal of Investigative Dermatology 89:119-120.
Inayama et al., "In Vitro and In Vivo Growth and Differentiation of Clones of Tracheal Basal Cells" Am. J. Pathol. 134(3):539-549 (Mar. 1989).
Inayama et al., "The Differentiation Potential of Tracheal Basal Cells" Lab. Invest. 58(6):706-717 (1988).
International Search Report dated Mar. 20, 2002, for PCT Application No. PCT/AU2002/00120, filed on Feb. 7, 2002, 2 pages.
International Search Report dated May 21, 2013, for PCT Application No. PCT/US2013/031316, filed on Mar. 14, 2013, 2 pages.
International Search Report dated Aug. 1, 2014, for PCT Application No. PCT/US2014/028944, filed on Mar. 14, 2014, 4 pages.
Jensen, et al., "Cultivation at Low Temperature as a Measure to Prevent Contamination with Fibroblasts in Epithelial Cultures from Human Skin," The Journal of Investigative Dermatology.
Jones and Elliget, "Method for the Culture of Human Bronchial Epithelial Cells from Tissues Obtained at Extended Postmortem Intervals" Annual Meeting Abstracts pp. 99 (Abstract).
Ke et al., "Cell Density Governs the Ability of Human Bronchial Epithelial Cells to Recognize Serum and Transforming Growth Factor Beta-I as Squamous Differentiation-inducing Agents" Am. J. Pathol. 137(4):833-843 (1990).
Kisker-Biotech dry block heat and water baths product catalog, 3 pages, printed May 3, 2002.

Lechner et al., "In Vitro Human Bronchial Epithelial Model Systems for Carcinogenesis Studies" In Vitro Models for Cancer Research. vol. VI Chapter 1 pp. 3-17.
Lechner et al., "Clonal Growth of Normal Adult Human Bronchial Epithelial Cells in a Serum-Free Medium" In Vitro 18(7):633-642 (Jul. 1982).
Lechner et al., "Induction of squamous differentiation of normal human bronchial epithelial cells by small amounts of serum" Differentiation 25:229-237 (1984).
Lee and Wood, "Management of Inhalation Injury" ANZBA (Manly) 0-34:39 (1998) (Abstract).
Lee et al., "An easy method for preparation of postage stamp autografts" Burns 26:741-749 (2000).
Liddiard et al., "Pressure Management of the Cultured Epithelial Auto graft" ANZBA (Canberra) p. 38 (1993) (Abstract).
Liddiard et al., "Scar management of the Cultured Epithelial Auto graft" ANZBA (Gold Coast) p. 37 (1995) (Abstract).
Liddiard et al., "The Direct Measurement of Cutaneous Pressure Generated by Pressure Garments" International Symposium on Hypertrophic Scars (Hong Kong) p. 36 (1995) (Abstract).
Lin et al., "Allogeneic microskin grafting of rabbits' skin wounds" Burns 19(3):208-214 (1993).
Lin et al., "Microskin grafting of rabbit skin wounds with Biobrane overlay" Burns 18(5):390-394 (1992).
Lindquist, et al. "The Heat-Shock Proteins"; Annu. Rev. Genet. 1988. 22: 631-77.
Ling (2000). Hyaluronan, Section II, Soft Tissue Repair by HA and HA Derivatives, Chapter XI. Postoperative Adhesion Prevention and Soft Tissue Repair by Hyaluronan, Hyaluronic Acid, Beijing, The China Light Industry Press, pp. 222-227 (with English translation).
Lucas, "Mini- and Micrografts Exclusively versus Standard Grafts Mixed with Mini- and Micrografts" p. 388 (1993) (Abstract).
Macdiarmid et al. (2001). "Separation of Epidermal Tissue from Underlying Dermis and Primary Keratinocyte Culture", Methods in Molecular Biology, vol. 174, pp. 401-410.
Magnusson and Wood, "Epidemiological Differences of Burn Injuries in Aboriginal and Nonaboriginal Children" ANZBA (Tasmania) p. 77 (1999) (Abstract).
Magnusson et al., "The Effect of Skin Graft Storage on Keratinocytes" ANZBA (Manly) Q-33:39 (1998) (Abstract).
Magnusson et al., "The Proliferative Capacity of Keratinocytes Isolated from Skin Stored After Meshing vs Non-Meshed" International Symposium on Hypertrophic Scars (Hong Kong) p. 51 (1999).
Magnusson et al., "Transepidermal Water Loss as a Quantitative Method for Evaluating Epithelialisation" ANZBA (Tasmania) p. 31 (1999) (Abstract).
Magnusson et al., "Transepidermal Water Loss as a Quantitative Method for Evaluating Epithelialisation." Princess Margaret Hospital for Children Res. Advances Seminar p. 50 (1999).
Mardovin et al., "Micrografts: The "Super" Expansion Graft" J. Burn Care Rehabil. 13 :556-559 (1992).
May et al., "Assessment of adhesion assays for use with keratinocytes" Exp. Dermatol. 10(1) :62-69 (2001).
Merriam-Webster Online Medical Dictionary definition of "suspension." <http://www2.merriam-webster.com/cgi- bin/mwmednlm?book=Medical&va=suspension>, accessed Sep. 2, 2008.
Merriam-Webster's College Dictionary p. 997, Random House (1991).
Mesenchymal Stem Cell—Wikipedia, the free encyclopedia, downloaded Sep. 30, 2016, 9 total pages.
Millipore (primary mesenchymal; pp. 1-2; downloaded on Oct. 3, 2016.
Mulekar, S., et al., "Treatment of vitiligo lesions by ReCell vs. conventional melanocyte-keratinocyte transplantation: a pilot study," The British Journal of Dermatology, 158(1):45-49, (Jan. 1, 2008).
Navarro F. A, et al., "Sprayed keratinocyte suspensions accelerate epidermal coverage in a porcine microwound model." J. Burn Care Rehabil. 21:513-518 (2000).
Neilson et al., "Case Presentation" ANZBA p. 71 (2000) (Abstract).
Nickoloff et al: "Further characterization of the keratinocyte somatomedin-C/insulin-like growth factor I receptor and the bio-

(56) References Cited

OTHER PUBLICATIONS logical responsiveness of cultured keratinocytes to SM-C/IGF-I", Dermatologica, vol. 177, No. 5, 1988 (265-273).
Noel-Hudson et al: "Human epidermis reconstructed on synthetic membrane: influence of experimental conditions on terminal differentiation", In Vitro Cell. Dev. Biol., 1995, vol. 31, No. 7 (508-515).
Zhang et al., "Microskin Grafting in the Treatment of Extensive Burns: A Preliminary Report" J. Trauma 28(6):804-807 (1988).
Non-Final Office Action dated Jul. 11, 2018, for U.S. Appl. No. 15/838,429, filed Dec. 12, 2017, 18 pages.
Zhang et al., "Microskin grafting. I. Animal experiments" Burns 12(8):540-543 (1986).
Non-Final Office Action in U.S. Appl. No. 10/068,299 dated Oct. 24, 2006.
Non-Final Office Action in U.S. Appl. No. 10/068,299 dated Dec. 28, 2007.
Non-Final Office Action in U.S. Appl. No. 10/068,299 dated Dec. 30, 2009.
Non-Final Office Action in U.S. Appl. No. 13/223,577 dated Jan. 11, 2012.
Non-Final Office Action in U.S. Appl. No. 13/223,577 dated Dec. 19, 2013.
Non-Final Office Action in U.S. Appl. No. 13/036,569 dated Oct. 11, 2011.
Non-Final Office Action in U.S. Appl. No. 13/036,569 dated Dec. 21, 2012.
Non-Final Office Action in U.S. Appl. No. 12/699,554 dated Apr. 10, 2012.
Non-Final Office Action in U.S. Appl. No. 12/699,554 dated Feb. 24, 2014.
Olsson et al, Leucoderma treated by transplantation of a basal cell layer enriched suspension British Journal of Dermatology 1998; 138:644-648.
Osborne et al: "Investigation into the biological stability of collagen/chondroitin-6-sulphate gels and their contraction by fibroblasts and keratinocytes: the effect of crosslinking agents and diamines", Biomaterials, vol. 20, No. 3, Feb. 1999 (283-290).
Papini and Wood, "Current concepts in the management of burns with inhalation injury" Care Crit. III. 15(2):61-66 (1999).
Papini et al., "Fluid Resuscitation Tissue Perfusion and Wound Salvage" ANZBA 0-30:37 (1998) (Abstract).
Papini et al., "Rapid Epithelial Cell Autograft" ANZBA (Manly) 0-31 :38 (1998) (Abstract).
Partial European Search Report dated Jun. 1, 2011, for EP Application No. 10 184 235.9, 4 pages.
Perrot et al., "Heel Pain—Repercussions for Functional Outcome in Major Burns" ANZBA (Manly) 0-29:37 (1998) (Abstract).
Petersen et al: "Enhanced synthesis of collagenase by human keratinocytes cultures on type I or type IV collagen", J. of Investigative Dermatology, vol. 94, No. 3, Mar. 1990 (341-346).
Product No. 352070 of BD e-Catalog: Centrifuges and test tubes, 3 pages, printed May 3, 2002.
Product No. 352360 of BD e-Catalog: Centrifuges and test tubes, 2 pages, printed May 3, 2002.
Pye (1988). "Cultured Keratinocytes as Biological Wound Dressings," Abstract, pp. 174-177.
Regnier M. et al. 1997. Integration of Langerhans cells into a pigmented reconstructed human epidermis. J Invest Dermatol 109: 510-512.
Robinson and Wu, "Culture of Conducting Airway Epithelial Cells in Serum-Free Medium" Tiss. Cult. Meth. 13:95-102 (1991).
Savandra and Wood, "The Influence of Surgery on the Genetic Predisposition to Form Hypertrophic Scars in the Paediatric Scald Population" ANZBA (Manly) 0-32:38 (1998) (Abstract).
Shimizu et al., "Expression of "Cell-type-specific" Markers during Rat Tracheal Epithelial Regeneration" Am. J. Respir. Cell Mal. Biol. 7:30-41 (1992).

Shore, J.W. et al. (1992). "Results of buccal mucosal grafting for patients with medically controlled ocular cicatricial pemphigoid," Ophthalmology 99:383-395.
Silla et al., "Milton Solution:" Does it have a place in burn treatment?ANZBA p. 52 (2000) (Abstract).
Skinner and Wood, "A Possible Alternative to Custom made Pressure Garments for Scar Manipulation" ANZBA (May 1994) (Abstract).
Skinner and Wood, "The Clinical Use of Hydrophobic Fabric Garments in the Paediatric Population" ANZBA p. 34 (1996) (Abstract).
Skinner et al., "Sunburn—An Unnecessary Cause of Pain" ANZBA (Queenstown) (1997) (Abstract).
Skinner et al., "The Comparison of Pressure Garment Implementation &Removal from 1991-1994" ANZBA (Gold Coast) p. 36 (1995) (Abstract).
Skouge, "Techniques for Split-Thickness Skin Grafting" J. Dermatol. Surg. Oncol. 13(8):841-849 (Aug. 1987).
Smith and Wood, "Heterotopic Ossification in Burns: Conservative and Surgical Management" ANZBA (Canberra) p. 20 (1993) (Abstract).
Smithwick and Wood, "Have Changes in Attitude to the Use of Blood Products Impacted Upon Their Use with the Treatment of a Patient with Major Burn Injury" ANZBA (Queenstown) (1997) (Abstract).
Smithwick and Wood, "Self Harm" ANZBA (Perth) (2000) (Abstract).
Smithwick and Wood, "The Impact of Major Orthopaedic Injuries on Burn Nursing Care" ANZBA (Gold Coast) p. 33 (1995) (Abstract).
Smithwick and Wood. (1994). "The impact of religious belief on the management of the burn injury" Presentation (Abstract).
Smithwick et al., "Stress Management in the Burn Unit" ANZBA (Canberra) p. 27(1993) (Abstract).
Solotoff, "Treatment for Pitted Acne Scarring—Postauricular Punch Grafts followed by Dermabrasion" J. Dermatol. Surg. Oncol. 12 (10):1079-1084 (Oct. 1986).
Sperring and Wood, "Continuing to Care—Burn Management in the Outpatient Setting" ANZBA p. 29 (1996) (Abstract).
Stoner and Wood, "Cultured Epithelial Auto graft Made Quick and Easy 1) Laboratory" ANZBA p. 41 (1996) (Abstract).
Stoner and Wood, "Systemic factors influencing the growth of cultured epithelial autograft" Burns 22(3):197-199 (1996).
Stoner and Wood, "The Treatment of Hypopigmentation with Cultured Epithelial Cell" ANZBA (Gold Coast) p. 32 (1995) (Abstract).
Stoner and Wood, "Treatment of Burns to the Sole of the Foot with Site Specific Cultured Epithelial Autograft" International Symposium on Hypertrophic Scars (Hong Kong) p. 14 (1995) (Abstract).
Stoner and Wood, "Treatment of burns to the sole of the foot with site specific cultured epithelial autograft" Presentation at the International Symposium on Hypertrophic Scar (Hong Kong) pp. 1-7 (1995) (Abstract).
Stoner and Wood, "Treatment of Burns to the Sole of the Foot with Site Specific Cultured Epithelial Autograft" ANZBA (Gold Coast) p. 17 (1995) (Abstract).
Stoner and Wood, "When It Absolutely, Positively Has to Be There!—The Logistics of Long Distance Transport of Cultured Epithelial Autograft" ANZBA (Tasmania) p. 64 (1999) (Abstract).
Stoner and Wood, "Why Use Cultured Epithelial Autograft as a Suspension?" ANZBA 0-39:41 (1998) (Abstract).
Stoner and Wood, 'Take' of Cultured Epithelial Auto graft Confirmed by the Presence of Cytokeratin 9" The Surgical Res. Soc. Australasia Ann. Sci. Meeting (Fremantle) (1997) (Abstract).
Stoner et al., "Cultured Airway Epithelium for the Treatment of Tracheal Burns" PAN/Asian European Tissue Repair Society Wound Healing Meeting (1997) (Abstract).
Stoner et al., "The Development of a Unique Technique of Cultured Epithelial Autograft Application" The Surgical Res. Soc. Australasia Ann. Sci. Meeting (Fremantle) ( 1997) (Abstract).
Stoner et al., "The Development of a Unique Technique of Cultured Epithelial Autograft Application" ANZBA (Queenstown) (1997) (Abstract).
Stoner et al., "The Treatment of Hypopigmented Lesions with Cultured Epithelial Autograft" J. Burn Care Rehabil. 21 (1):50-54 (2000).

(56) References Cited

OTHER PUBLICATIONS

Stoner et al., "The Use of Epithelial Cell Suspension with Meshed Split-Thickness Autograft Using Un-Cultured Keratinocytes in a Pig Model" ANZBA (Tasmania) p. 63 (1999) (Abstract).
Svensjo T., et al., "Autologous keratinocyte suspensions accelerate epidermal wound healing in pigs." J. Surgical Res. 99:211-221 (2001).
Tan et al., "The Management of Paediatric Palm Burn Injuries" ANZBA p. 65 (1996) (Abstract).
Teepe et al., "Fresh versus cryopreserved cultured allografts for the treatment of chronic skin ulcers" Brit. J. Dermatol. 122:81-89 (1990).
The current uses of cultured epidermis in Perth and its possible future. Royal Australasian College of Surgeons, Scientific Meeting (1992) (Abstract).
Vollberg et al., "Identification of Multiple Stages in the Program of Squamous Differentiation in Tracheobrochial Epithelial Cells" 1984.
Wenkel, H. et al. (2000). "Long term results after autologous nasal mucosal transplantation in severe mucus deficiency syndromes," British Journal of Ophthalmology 84:279-284.
Wheeland, "The Technique and Current Status of Pinch Grafting" J. Dermatol. Surg. Oncol. 13(8):873-880 (Aug. 1987).
Williams, "Intensive Care Burns—An Experience" ANZBA PL-5:23 (1998) (Abstract).
Wood and Caldow, "Advances in Burn Care Over 30 Years at Royal Perth Hospital" ANZBA p. 70 (1996) (Abstract).
Wood and Stoner, "Implication of basement membrane development on the underlying scar in partial-thickness burn injury" Burns 22(6):459-462 (1996).
Wood and Stoner, "The Clinical Use of Integra for Dermal Reconstruction" Tissue Engineering Meeting (Orlando) (1999) (Abstract).
Wood and Stoner, "The Implication of Basic Membrane Development on the Underlying Scar in Partial Thickness Burn Injury" International Symposium on Hypertrophic Scars (Hong Kong) p. 28 (1995) (Abstract).
Wood and Stoner, "The Use of Cultured Epithelial Autograft in Paediatric Burn Management" European Club for Paediatric Burns. Scientific Sessions (Zurich) (1996) (Abstract).
Wood and Stoner, "Western Australian Skin Culture Unit—A 5 Year Review" Tissue Engineering Meeting (Orlando) (1999) (Abstract).
Wood et al., "Augmented Clinical Assessment of Burn Injuries: Do You Believe What You See?" ANZBA (Queenstown) (1997) (Abstract).
Wood et al., "Current difficulties and the possible future directions in scar assessment" Burns 22(6):455-458 (1996).
Wood et al., "Scar management of cultured epithelial autograft" Burns 22(6):451-454 (1996).
Wood et al., "Scar Management of the Cultured Epithelial Autograft" International Symposium on Hypertrophic Scars (Hong Kong) p. 19 (1995) (Abstract).
Wood et al., "The Current Difficulties and the possible future direction in scar assessment" International Symposium on Hypertrophic Scars (Hong Kong) p. 20 (1995) (Abstract).
Wood et al., "The Role of Integra Dermal Template in Scar Reconstruction Post Burn Injury" ANZBA (Tasmania) p. 79 (1999) (Abstract).
Wood et al., "Wound Bed Preparation with Dermal Preservation" ANZBA (1996) (Abstract).
Wood, "Advances in the use of cultured skin in wound care" Second Australian Wound Management Association (1998) (Abstract).
Wood, "Clinical Indications for the Use of Integra" ANZBA (1997) (Abstract).
Wood, "Dermal reconstruction in the repair of full thickness skin loss" The Second Australian Wound Management Association Conference (Queensland) (1998) (Abstract).
Wood, "Dermal Replacement for Use with Cultured Epidermal Autograft" ANZBA (Canberra) p. 36 (1993) (Abstract).
Wood, "Early Burn Excision" Oral Presentation. Indonesian Surgeons Association Congress pp. 1-4 (Jul. 1996) (Abstract).
Wood, "Experience of the First Two Years of the Skin Culture Laboratory in Western Australia" ANZBA (Gold Coast) p. 10 (1995) (Abstract).
Wood, "Facial Burn Management" ANZBA (Queenstown) (1997) (Abstract).
Wood, "Facial Burn Management" PAN/Asian European Tissue Repair Society Wound Healing Meeting (1997) (Abstract).
Wood, "Integra 12 Months On." ANZBA (Manly) 0-38 (1998) (Abstract).
Wood, "Long distance wound care" Second Australian Wound Management Association (1998) (Abstract).
Wood, "Major Burns Disaster Plan" ANZBA (Tasmania) p. 66 (1999) (Abstract).
Wood, "Quality assurance in burn patient care: the James Laing Memorial Essay, 1994" Burns 21 (8):563-568 (1995).
Wood, "Skin Grafting to Achieve Minimal Scarring" ANZBA (Canberra) p. 40 (1993) (Abstract).
Wood, "Tailored Wound Healing" ANZBA (Tasmania), p. 30 (1999) (Abstract).
Wood, "Teamwork" ANZBA (Manly) PL-6:23 (1998) (Abstract).
Wood, "The Clinical Indications for the Use of Cultured Epithelial Auto grafts" Oral Presentation at the Indonesian Surgeons Association Congress p. 1-4 (Jul. 1996) (Abstract).
Wood, "The Ethics of Burn Care" ANZBA (Manly) 0-36-38:40 (1998) (Abstract).
Wood, "The First Four Years of the Skin Culture Laboratory in W.A" The Surgical Res. Soc. Australasia Ann. Sci. Meeting (Fremantle) (1997) (Abstract).
Wood, "The Use of Tissue Culture Techniques for the Treatment of the Partial Thickness Burn Injury" Primary Intent. (Australia) 1 (1):16-17 (Nov. 1993).
Wright and Wood, "The Use of Intranasal Fentanyl PCA for Pain Control During Burn Wound Dressing Change" ANZBA p. 60 (1996) (Abstract).
Written Opinion of the International Searching Authority dated May 21, 2013, for PCT Application No. PCT/US2013/031316, filed on Mar. 14, 2013, 6 pages.
Written Opinion of the International Searching Authority dated Aug. 1, 2014, for PCT Application No. PCT/US2014/028944, filed on Mar. 14, 2014, 5 pages.
Wu and Stoner, "Cultured Epithelial Autograft Made Quick and Easy 2) Surgery" ANZBA p. 42 (1996) (Abstract).
Wu et al., "Growth and differentiation of human nasal epithelial cells in culture. Serum-free, hormone-supplemented medium and proteoglycan synthesis" Am. Rev. Resp. Dis. 132(2):311-320 (1985) (Abstract).
Wu, Y. et al (2007). "Mesenchymal Stem Cells Enhance Wound Healing Through Differentiation and Angiogenesis," Stem Cells 25:2648-2659.
Wyle and Wood, "Sensation Following Integra Dermal Replacement of Full Thickness Burns" ANZBA (Tasmania) p. 83 (1999) (Abstract).
Young, A, et al., "Human Melanocytes and Keratinocytes Exposed to UVB or UVA In Vivo Show Comparable Levels of Thymine Dimers," The Journal of Investigative Dermatology, 11(6):936-940.
Final Office Action dated Jun. 21, 2019, for U.S. Appl. No. 14/386,519, filed Sep. 19, 2014, 14 pages.
Harvey et al. (1985). "Blood, fluids, electrolytes, and hematologic drugs," Chapter 42 in Remington's Pharmaceutical Sciences, 17$^{th}$ Edition; Gennaro et al., ed., Mack Publishing Company: Easton, PA, pp. 816-842.
Non-Final Office Action dated Feb. 28, 2019, for U.S. Appl. No. 14/386,519, filed Sep. 19, 2014, 14 pages.
Non-Final Office Action dated Aug. 7, 2019, for U.S. Appl. No. 16/436,693, filed Jun. 10, 2019, 21 pages.
Suri, S. et al. (2009). "Photopatterned collagen-hyaluronic acid interpenetrating polymer network hydrogels," Acta Biomaterialia 5:2385-2397.

* cited by examiner

SYSTEMS AND METHODS FOR TISSUE PROCESSING AND PREPARATION OF CELL SUSPENSION THEREFROM

CROSS REFERENCE TO RELATED APPLICATIONS

This application is a national phase filing under 35 U.S.C. 371 of International Application No. PCT/US2014/028944 filed Mar. 14, 2014, which claims the benefit of and priority to U.S. Provisional App. No. 61/783,422 filed Mar. 14, 2013 and Australian App. No. 2013205148 filed Apr. 13, 2013, all of which applications are hereby incorporated by reference in their entirety.

FIELD OF THE INVENTION

This invention relates to an at least partially automated device and its use for preparing a cell suspension, particularly a suspension comprising viable epithelial cells useful in tissue regeneration.

BACKGROUND

Tissue regeneration in humans is extremely limited and constitutes a major challenge to the repair of damaged organ function. Wound treatment is a typical area where tissue regeneration is required. Wounds (lacerations or openings) in mammalian tissue can result in tissue disruption and coagulation of the microvasculature at the wound face. Repair of such tissue represents an orderly, controlled cellular response to injury. All soft tissue wounds, regardless of size, heal in a similar manner. The mechanisms of tissue growth and repair are biologic systems wherein cellular proliferation and angiogenesis occur in the presence of an oxygen gradient. The sequential morphological and structural changes, which occur during tissue repair have been characterized in great detail and have, in some instances, been quantified. See Hunt, T. K., et al., "Coagulation and macrophage stimulation of angiogenesis and wound healing," The surgical wound, pp. 1-18, ed. F. Dineen & G. Hildrick-Smith (Lea & Febiger, Philadelphia: 1981).

Tissue regeneration in various organs, such as the skin or the heart depends on connective tissue restoring blood supply and enabling residual organ-specific cells such as keratinocytes or muscle cells to reestablish organ integrity. Thus, a relevant function of the mesenchymal cells, e.g., the fibroblasts or, in addition, the endothelial cells of vasculature, is secretion of factors enhancing the healing process, e.g., factors promoting formation of new blood vessels (angiogenesis) or factors promoting re-epithelialization by proliferating and migrating keratinocytes.

The cellular morphology of a wound consists of three distinct zones. The central avascular wound space is oxygen deficient, acidotic and hypercarbic, and has high lactate levels. Adjacent to the wound spate is a gradient zone of local ischemia, which is populated by dividing fibroblasts. Behind the leading zone is an area of active collagen synthesis characterized by mature fibroblasts and numerous newly formed capillaries (i.e., neovascularization). While new blood vessel growth (angiogenesis) is necessary for the healing of wound tissue, angiogenic agents generally are unable to fulfill the long-felt need of providing the additional biosynthetic effects of tissue repair. In addition to acute wound (e.g., burn or laceration caused by trauma), artificially created wound (e.g., in a graft donor site, aesthetic indication, plastic procedure or definal treatment), chronic wound (e.g., venous or diabetic ulcers) and other indications such scar remodeling, glabrous skin loss injuries, pigmentation issues, vitiligo, leucoderma and cosmetic rejuvenation procedures also require rapid and efficient therapeutics. Despite the need for more rapid healing of wounds (e.g., severe burns, surgical incisions, lacerations and other trauma), to date there has been only limited success in accelerating wound healing with pharmacological agents.

The primary goal in the conventional treatment of wounds is to achieve wound closure. Open cutaneous wounds represent one major category of wounds. This category includes acute surgical and traumatic, e.g., chronic ulcers, burn wounds, as well as chronic wounds such as neuropathic ulcers, pressure sores, arterial and venous (stasis) or mixed arterio-venous ulcers, and diabetic ulcers. Open cutaneous wounds routinely heal by a process comprising six major components: i) inflammation, ii) fibroblast proliferation, iii) blood vessel proliferation, iv) connective tissue synthesis, v) epithelialization, and vi) wound contraction. Wound healing is impaired when these components, either individually or as a whole, do not function properly. Numerous factors can affect wound healing, including malnutrition, infection, pharmacological agents (e.g., cytotoxic drugs and corticosteroids), diabetes, and advanced age. See Hunt et al., in *Current Surgical Diagnosis & Treatment* (Way; Appleton & Lange), pp. 86-98 (1988).

Skin wounds that do not readily heal can cause the subject considerable physical, emotional, and social distress as well as great financial expense. See, e.g., Richey et al., *Annals of Plastic Surgery* 23(2):159-65 (1989). Indeed, wounds that fail to heal properly finally may require aggressive surgical treatments such as autologous skin grafting (where sheets of skin are grafted) or cultured dermis grafting. For example, cultured epithelial autograft (CEA) procedures take skin cells from the patient to grow new skin cells in sheets in a laboratory. The new sheets are used as grafts. However, the take rate of these grafts is not satisfactory. See, e.g., Sood et al., *Journal of Burn Care Research* 31(4):559-68 (2010). Newer grafting procedures combine CEA with a matrix for more support. For example, currently available as cultured or engineered dermis are products having different matrices into which fibroblasts are incorporated, such as TransCyte® and Dermagraft®. However, these products are not efficient in inducing epithelialization in large wounds. Cultured/engineered skin incorporating epidermal cells and fibroblasts are available as Apligraf® (NOVARTIS Pharma) and VivoDerm® (Bristol-Myers Squibb). However, there are problems regarding the affinity between cultured epidermal layer and dermal layer, and insufficiency in clinical effect obtainable.

A need for improved wound healing, and more broadly, tissue regeneration technique exists. The present invention provides an autologous cellular suspension suitable for application on various recipient sites, which can be used without regard to the type or tissue of the wound or the nature of the patient population. Automated devices and use thereof for preparing said suspension are also provided.

SUMMARY OF THE INVENTION

In one aspect, an automated system for cell harvesting and transplant is provided. The system includes:
  a disposable cartridge for processing a tissue, comprising
    a tissue processing chamber, a disintegrator situated therein and a cell collection chamber separated from the tissue processing chamber by the disintegrator, wherein after dissociating the tissue in the tissue processing chamber mechanically and/or chemically and passing the dissociated tissue through the disintegrator, a cell suspension is collected in the cell collection chamber;

optionally, a disposable applicator removably in fluid communication, directly or indirectly, with the cell collection chamber and capable of receiving the cell suspension therefrom; and a reusable console for housing the cartridge and the applicator and for providing motive power to supply a mechanical force and/or a chemical reagent to the tissue, the console comprising an actuating mechanism for actuating a disintegrating member so as to exert a mechanical force on the tissue placed in the tissue processing chamber, thereby mechanically dissociating the tissue.

In some embodiments, the cartridge is sealed in a sterile packaging before use. The disintegrator can be a mesh, screen, grid, blade, or any combination thereof. In some designs, the cartridge further comprises a cap removably placed on or hinged to the tissue processing chamber for engaging the actuating mechanism, wherein the cap has a seal for sealing the tissue processing chamber. For example, the seal on a first side facing the tissue processing chamber can have a working surface, wherein when the disintegrating member is actuated and placed upon a second side of the seal facing the disintegrating member, the working surface is in contact with the tissue placed in the tissue processing chamber. The cartridge can further comprise a locking mechanism for securing the cap once placed on the tissue processing chamber, such that the cap remains placed when the system is in use.

In various embodiments, the cartridge further comprises a first packet for providing an enzyme solution and a second packet for providing a buffer solution, both packets in fluid communication with the tissue processing chamber, wherein the enzyme solution breaks down extracellular matrix in the tissue thereby chemically dissociating the tissue, and wherein the buffer solution washes the dissociated tissue and suspends cells in the cell suspension. For example, the first packet can have a first and a second container separated by a breakable seal, the first container containing sterile water and the second container containing lyophilized enzyme powder, wherein when the seal is broken, the lyophilized enzyme powder meets the sterile water and dissolves therein. Such first or second container can be a pouch, a vial or a syringe. To deliver the reagents to the tissue, the console can further comprise a first pressurizing mechanism for driving the enzyme solution and a second pressurizing mechanism for driving the buffer solution out of the first packet and the second packet, respectively, into the tissue processing chamber. In some embodiments, the first packet further collects waste enzyme solution after use and the second packet further collects waste buffer solution after use. All waste can be collected in one packet as well. The first packet can be in fluid communication with a first pump for pumping the enzyme solution and the waste enzyme solution. The second packet can also be in fluid communication with a second pump for pumping the buffer solution and the waste buffer solution. In some embodiments, the cartridge further comprises a pump for drawing the cell suspension from the cell collection chamber, and subsequently after filled, pumping the cell suspension into the applicator, the third pump in fluid communication with the cell collection chamber and the applicator. Two or all of the first, second and third pumps can be the same pump. The first, second, or third pump may be peristaltic, syringe, or other type of pump and may be disposable or reusable. In some embodiments, the cartridge further comprises a first syringe for collecting waste enzyme solution and a second syringe for collecting waste buffer solution, both syringes in fluid communication with the cell collection chamber. The cartridge can also further comprise a third syringe for drawing the cell suspension from the cell collection chamber, and subsequently after filled, pumping the cell suspension into the applicator, the third syringe in fluid communication with the cell collection chamber and the applicator. In certain embodiments, the cartridge further comprises a fluid detector for controlled metering of the enzyme solution and the buffer solution. As an alternative to the pouches, the cartridge can include three containers for providing an enzyme solution, sterile water and lyophilized enzyme powder, respectively.

In certain embodiments, small amounts of the enzyme solution can be pumped in and out of the chamber during incubation (e.g., at fixed intervals or frequency), to help agitate the enzyme solution and accelerate tissue processing/disintegration.

In various embodiments, the cartridge may further comprise at least one supplying container for providing an exogenous agent. The supplying container can be the same packet for providing the buffer solution (e.g., the buffer solution can include the exogenous agent or be replaced with a solution of the exogenous agent after release of the buffer solution from the packet). The exogenous agent can be, for example, a heat shock protein or a fragment thereof, hyaluronic acid, platelet-enriched plasma, a growth factor, adipose stem cells, or any combination of the foregoing.

In certain embodiments, the cartridge further comprises a filter situated between the disintegrator and the cell collection chamber, for filtering the processed tissue to remove large aggregates. A filter can be alternatively or additionally situated between the cell collection chamber and the applicator, for filtering the cell suspension to remove large aggregates.

In some embodiments, the cartridge further comprises a mechanism for balancing pressure during fluid movement, which may be an antimicrobial filter or a bore tortuous path.

Where desirable or required, one or more components of the cartridge in contact with a biological material is removably assembled therein so that such component can be removed from the cartridge for biohazard disposal allowing the rest of the cartridge to be recycled.

The applicator can be a part of the system or a stand-alone device. An outer surface of the applicator can be sealed in a sterile packaging before transport to a sterile field for cell transplant. In some embodiments, the applicator is capable of dispensing, spraying or dripping the cell suspension therein onto a recipient site or a support. The applicator may be pressurized or spring-loaded. The applicator may have a pivoting head for axial application of the cell suspension. As an alternative or in addition to the applicator, the system can include a support or substrate for receiving the cell suspension, wherein the support, after receiving the cell suspension, is presented for transplant or culturing. The support may be a matrix, a scaffold, a dressing, or any combination thereof; the support may be solid, semi-solid, porous or fragmented.

In various embodiments, the disintegrating member may be part of the console (e.g., connected to the actuating mechanism) or part of the cartridge (e.g., situated in the tissue processing chamber and, e.g., connected to the cap). The disintegrating member can be a pestle or grinder. In some embodiments, where a pestle is used, the pestle may cycle up and down and/or rotate to promote tissue processing. The pestle can also have one or more fins.

In some embodiments, the console further comprises one or more of: a mechanism for drawing and ejecting the cartridge into or out of the console; an interlock to prevent removal of the cartridge during processing; an operator interface to control processing time, suspension volume needed, and activation of tissue processing; a display panel showing status of tissue processing; and an ejecting mechanism for ejecting the applicator when filled.

In various embodiments, the system may include a custom control software for directing a processor or computer chip in the console to control the automated process. The system may also be connected to an external computer for collecting and processing data.

In addition to the console, the cartridge may also have a mechanism for providing power (e.g., heat) so as to supply a mechanical force and/or a chemical reagent to the tissue.

In another aspect, a system for cell harvesting and transplant can include:
  a cartridge for processing a tissue, comprising a tissue processing chamber, a disintegrator situated therein and a cell collection chamber separated from the tissue processing chamber by the disintegrator, wherein after dissociating the tissue placed in the tissue processing chamber mechanically and/or chemically and passing the dissociated tissue through the disintegrator, a cell suspension is collected in the cell collection chamber; and
  a programmable console for housing the cartridge and for providing motive power to supply a mechanical force and/or a chemical reagent to the tissue, wherein the console comprises a processor for controlling the console to supply the mechanical force and/or chemical reagent.

In certain embodiments, the tissue can be an at least partially processed tissue sample prior to being placed in the cartridge. For example, the at least partially processed tissue sample has been subject to incubation with an enzyme so as to break down extracellular matrix in the tissue thereby chemically dissociating the tissue.

In various embodiments, the cartridge can further comprise a container for providing a solution comprising the chemical reagent, wherein the chemical reagent is capable of breaking down extracellular matrix in the tissue. Correspondingly, the console further comprises a pressurizing mechanism for driving the solution out of the container and into the tissue processing chamber, thereby chemically dissociating the tissue therein.

In some embodiments, the cartridge can be sealed in a sterile packaging before use. The cartridge can further comprise a cap removably placed on or hinged to the tissue processing chamber for engaging the actuating mechanism, wherein the cap has a seal for sealing the tissue processing chamber. In one embodiment, the seal on a first side facing the tissue processing chamber has a working surface, wherein when the disintegrating member is actuated and placed upon a second side of the seal facing the disintegrating member, the working surface is in contact with the tissue placed in the tissue processing chamber. In some embodiments, the cartridge further comprises a locking mechanism for securing the cap once placed on the tissue processing chamber, such that the cap remains placed when the system is in use.

In some embodiments, the cartridge further comprises at least one supplying container for providing an exogenous agent, which can be a heat shock protein or a fragment thereof, hyaluronic acid, platelet-enriched plasma, a growth factor, adipose stem cells, or any combination of the foregoing.

In certain embodiments, the console further comprises a disintegrating member and an actuating mechanism therefor, wherein when actuated, the disintegrating member engages with the tissue processing chamber and exerts the mechanical force on the tissue placed therein, thereby mechanically dissociating the tissue. In some embodiments, the cartridge further comprises a disintegrating member situated in the tissue processing chamber. The disintegrating member can be a pestle or grinder, and the disintegrator (in the cartridge) can be a mesh, screen, grid, blade, or any combination thereof.

As an alternative or in addition to the disintegrating member and the actuating mechanism, the console can further comprise a magnetic source for driving movement of a magnet placed in the tissue processing chamber, wherein movement of the magnet exerts the mechanical force on the tissue placed therein, thereby mechanically dissociating the tissue.

The system optionally further comprises a disposable applicator removably in fluid communication, directly or indirectly, with the cell collection chamber and capable of receiving the cell suspension therefrom. The applicator is capable of dispensing, spraying or dripping the cell suspension therein onto a recipient site or a support. As an alternative or in addition to the applicator, the system can include a support for receiving the cell suspension, wherein the support, after receiving the cell suspension, is presented for transplant or culturing. The support may be a matrix, a scaffold, a dressing, or any combination thereof; the support may be solid, semi-solid, porous or fragmented.

The system can further include a filter situated between the disintegrator and the cell collection chamber, for filtering the processed tissue to remove large aggregates. A filter can also be situated after the cell collection chamber, for filtering the cell suspension to remove large aggregates.

In some embodiments, one or more components of the cartridge in contact with a biological material can be removably assembled therein so that such component can be removed from the cartridge for biohazard disposal allowing the rest of the cartridge to be recycled.

In various embodiments, the system may include a custom control software for directing a processor or computer chip in the console to control the automated process. The system may also be connected to an external computer for collecting and processing data.

In addition to the console, the cartridge may also have a mechanism for providing motive power (e.g., heat) so as to supply a mechanical force and/or a chemical reagent to the tissue.

Methods of cell harvesting and transplant using the system described herein are also provided. The method can comprise:
  placing the tissue in the tissue processing chamber;
  directing the console to actuate the disintegrating member; and
  retrieving the applicator having the cell suspension therein.

In some embodiments, the method includes:
  placing the tissue in the tissue processing chamber;
  directing the processor in the console so as to supply the mechanical force and/or chemical reagent to the tissue; and
  retrieving the cell suspension.

In various embodiments, in the method of cell harvesting and transplant above, the tissue has been subject to incubation with an enzyme so as to break down extracellular matrix in the tissue thereby chemically dissociating the tissue.

Other aspects and advantages of the invention will become apparent to those skilled in the art from the ensuing description.

--BRIEF DESCRIPTION OF THE DRAWINGS

FIG. 16 illustrates a workflow for the OR.

DETAILED DESCRIPTION

Figure 1:
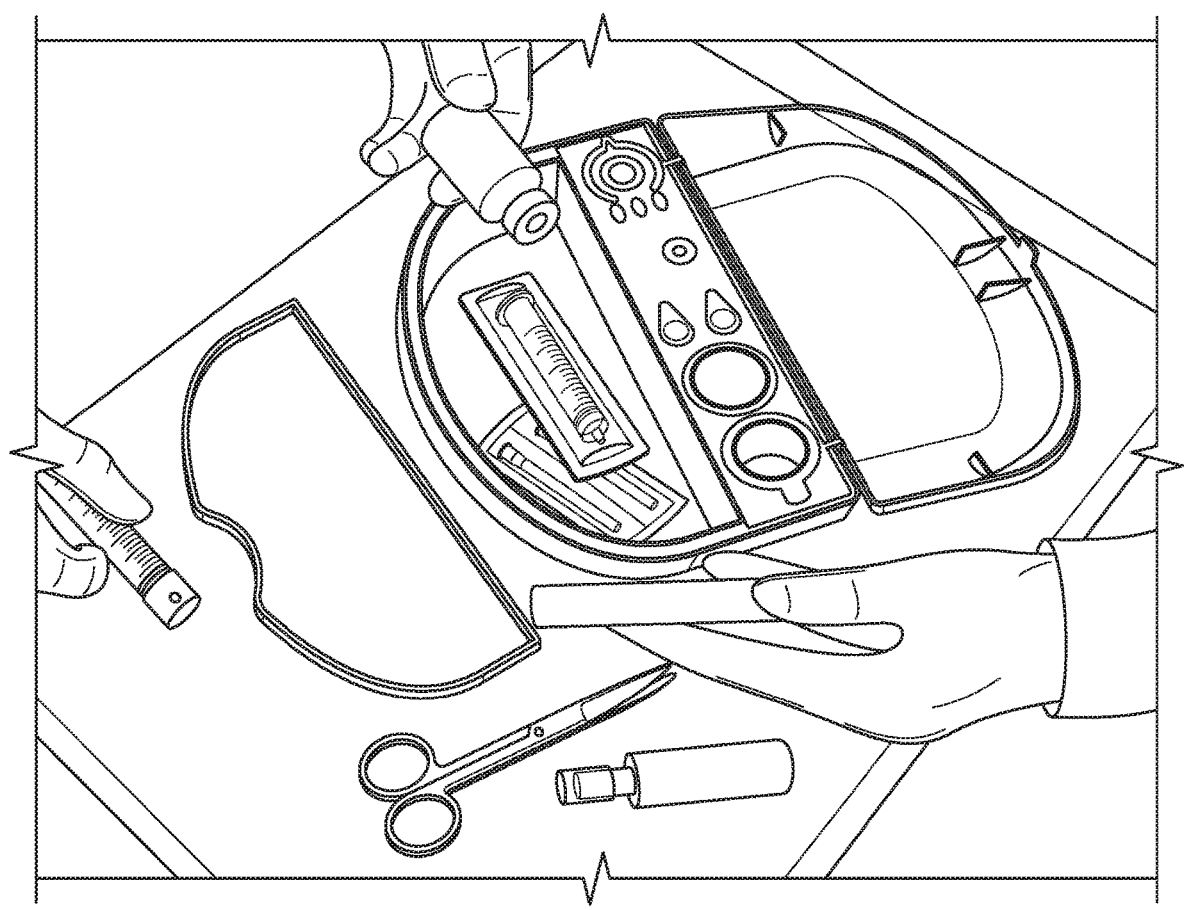
FIG. 1 shows the manual ReCell Kit.
Figure 2A:
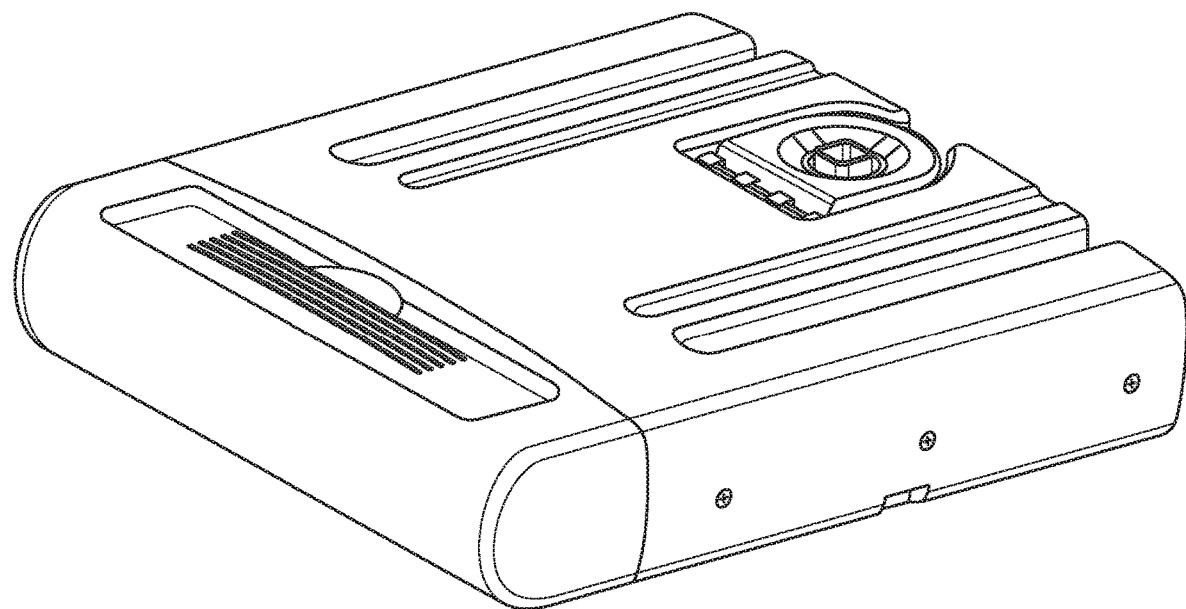
FIGS. 2A-3B illustrate two different designs of a disposable Cartridge or Cassette.
Figure 2B:
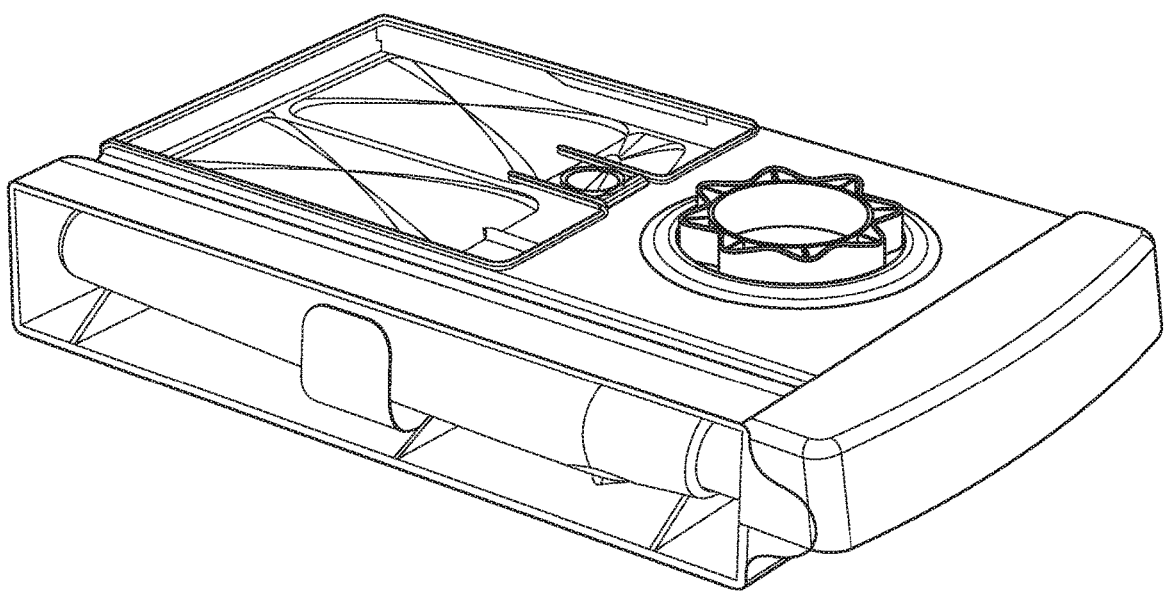
Figure 3A:
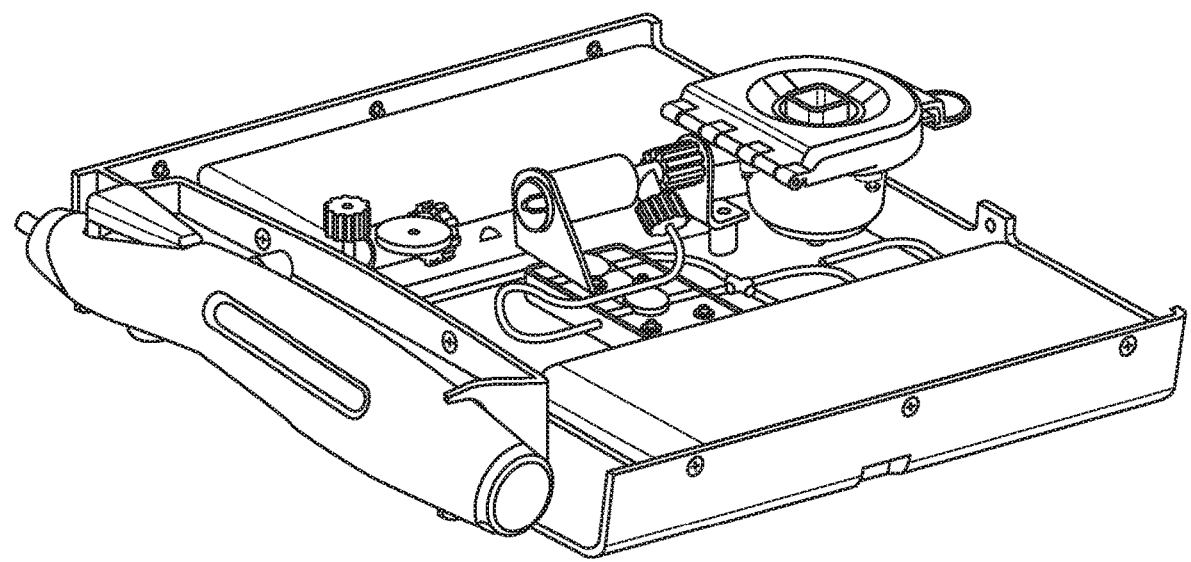
Figure 3B:
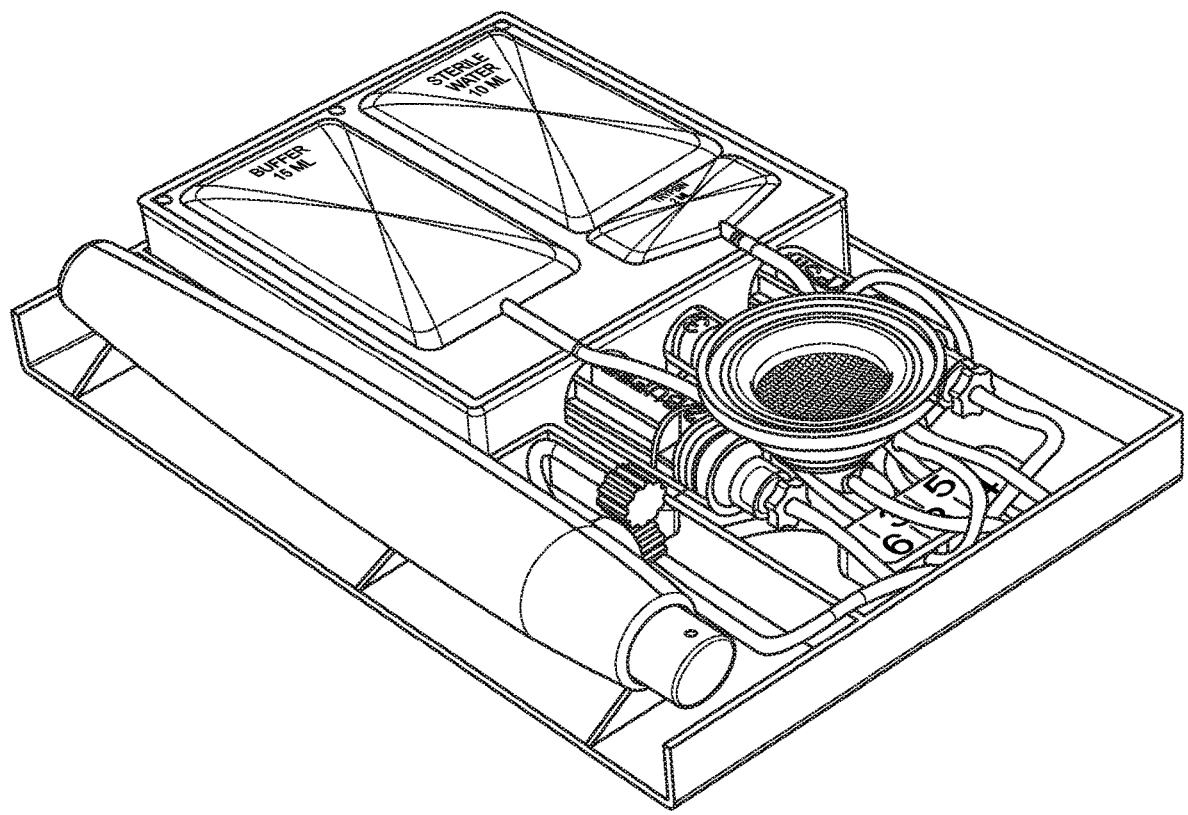
Figure 4A:
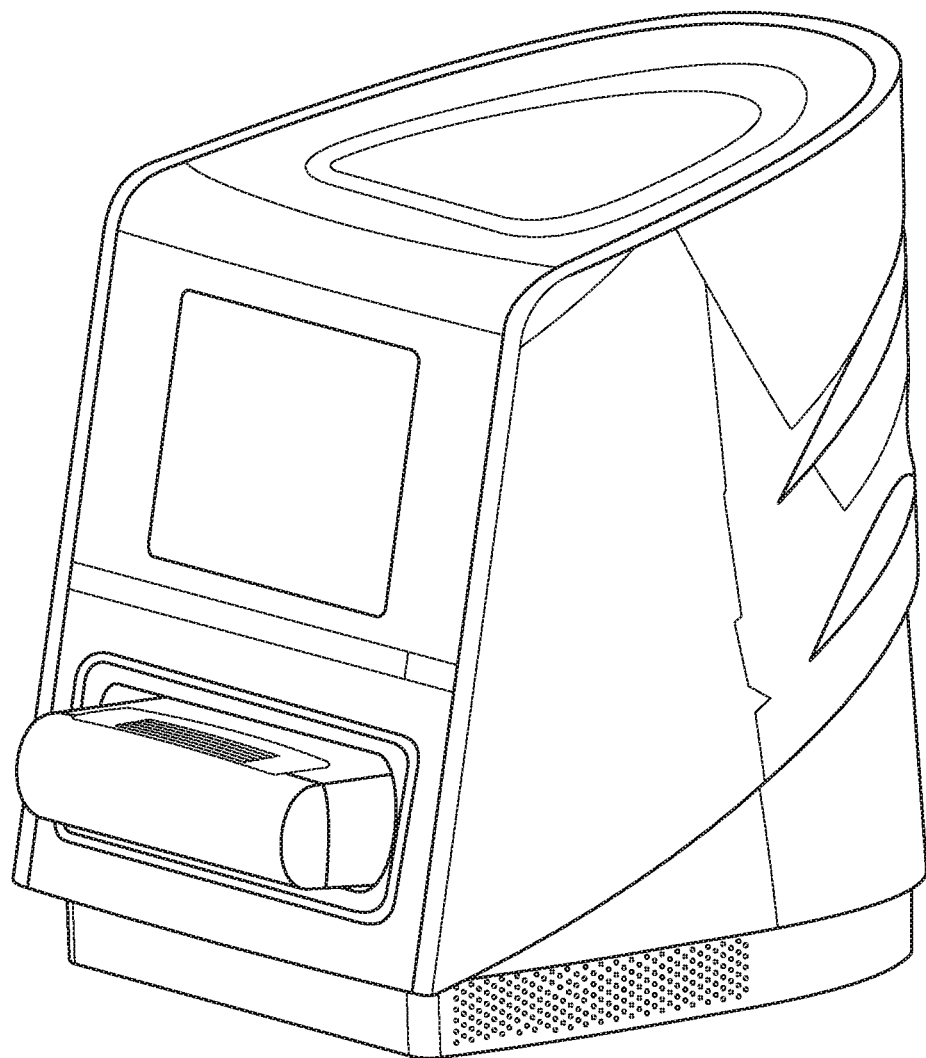
FIGS. 4A-6B illustrate two different designs of a reusable Console.
Figure 4B:
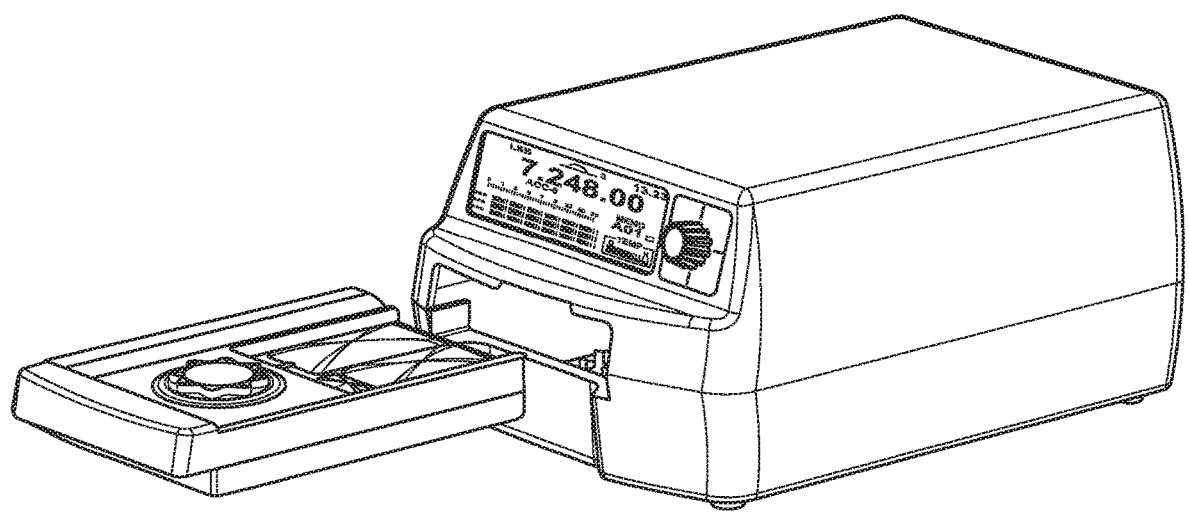
Figure 5A:
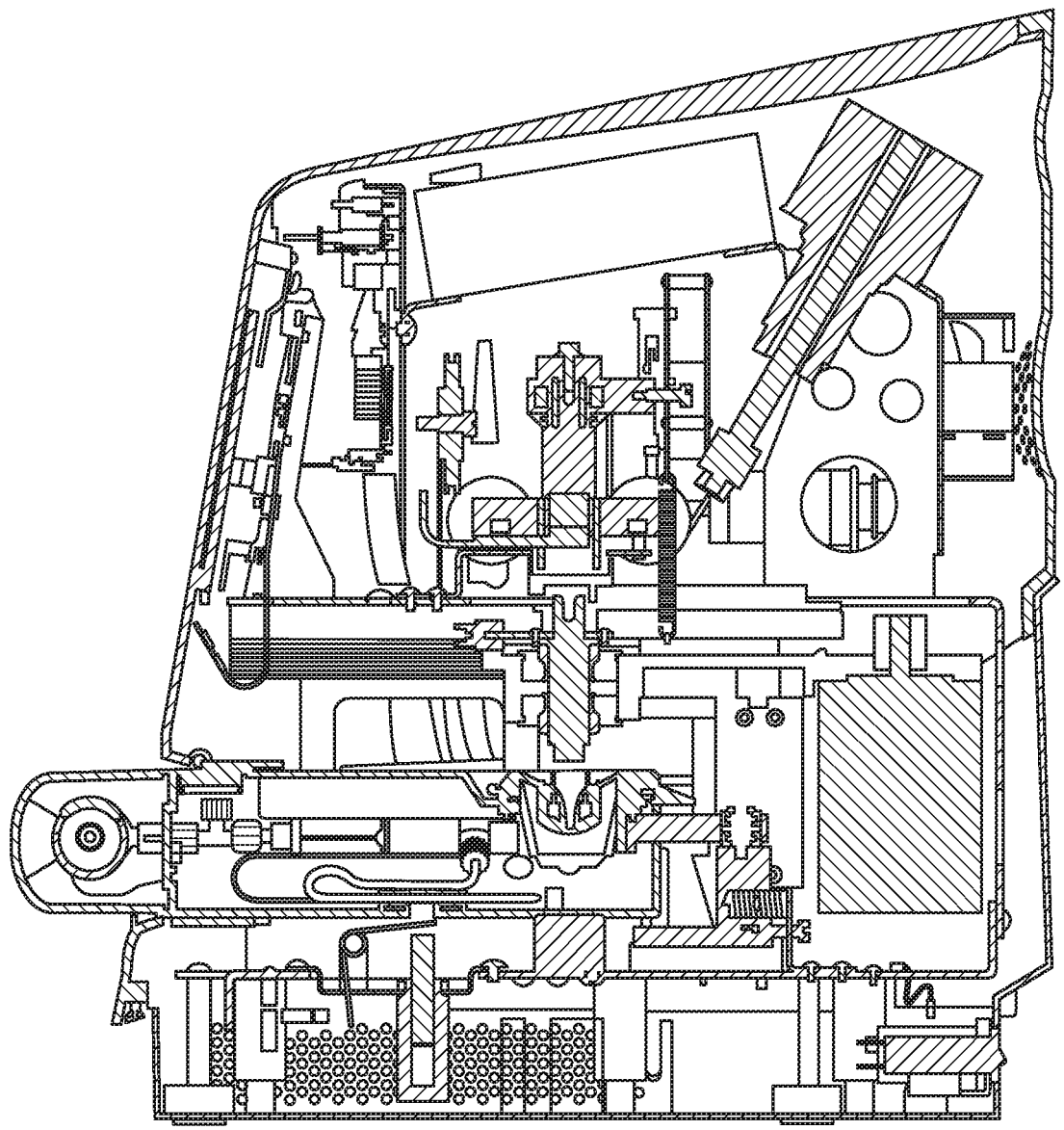
Figure 5B:
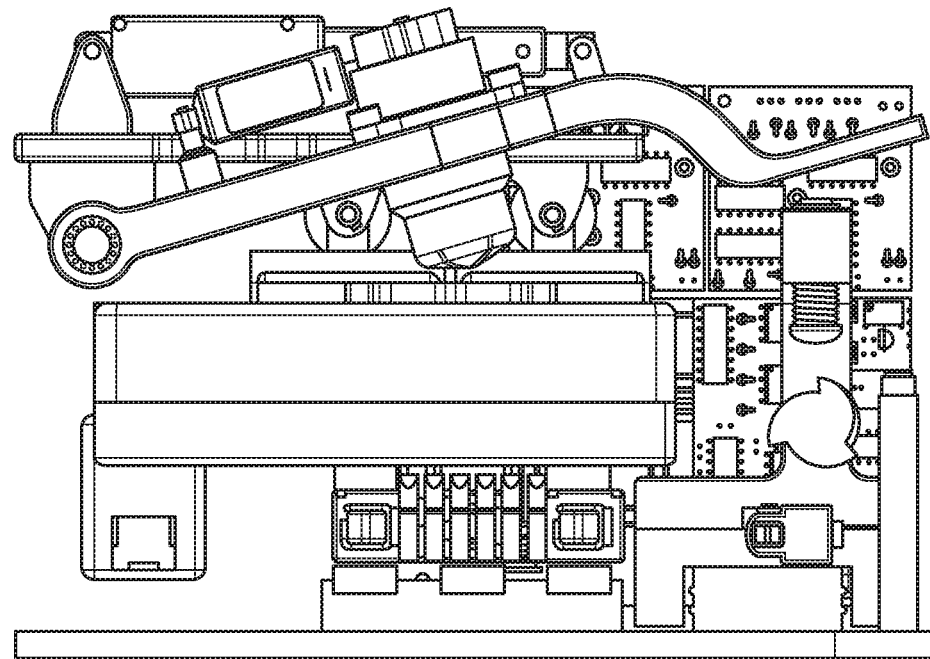
Figure 5B:
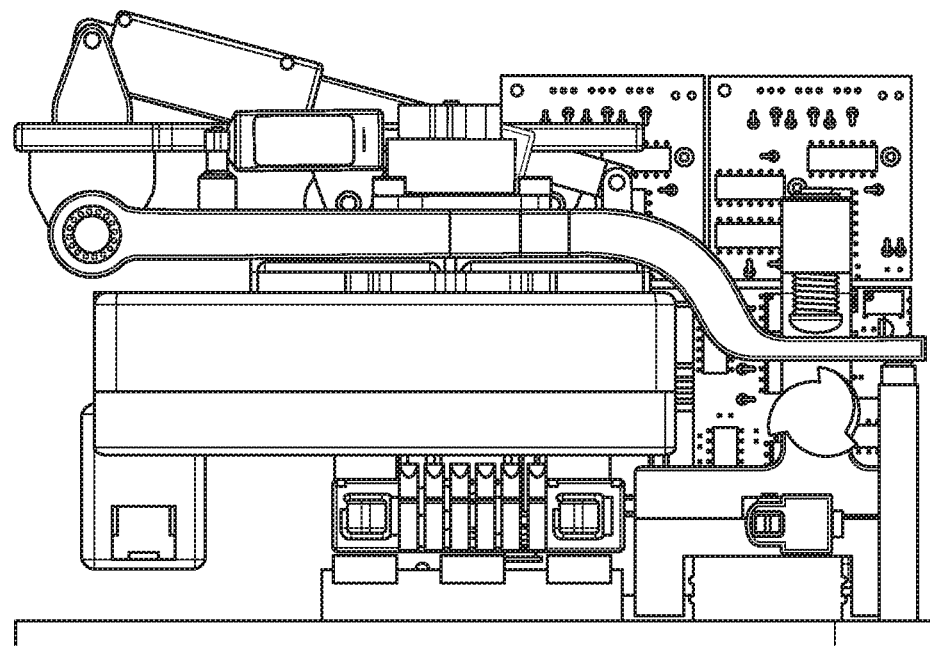
Figure 6A:
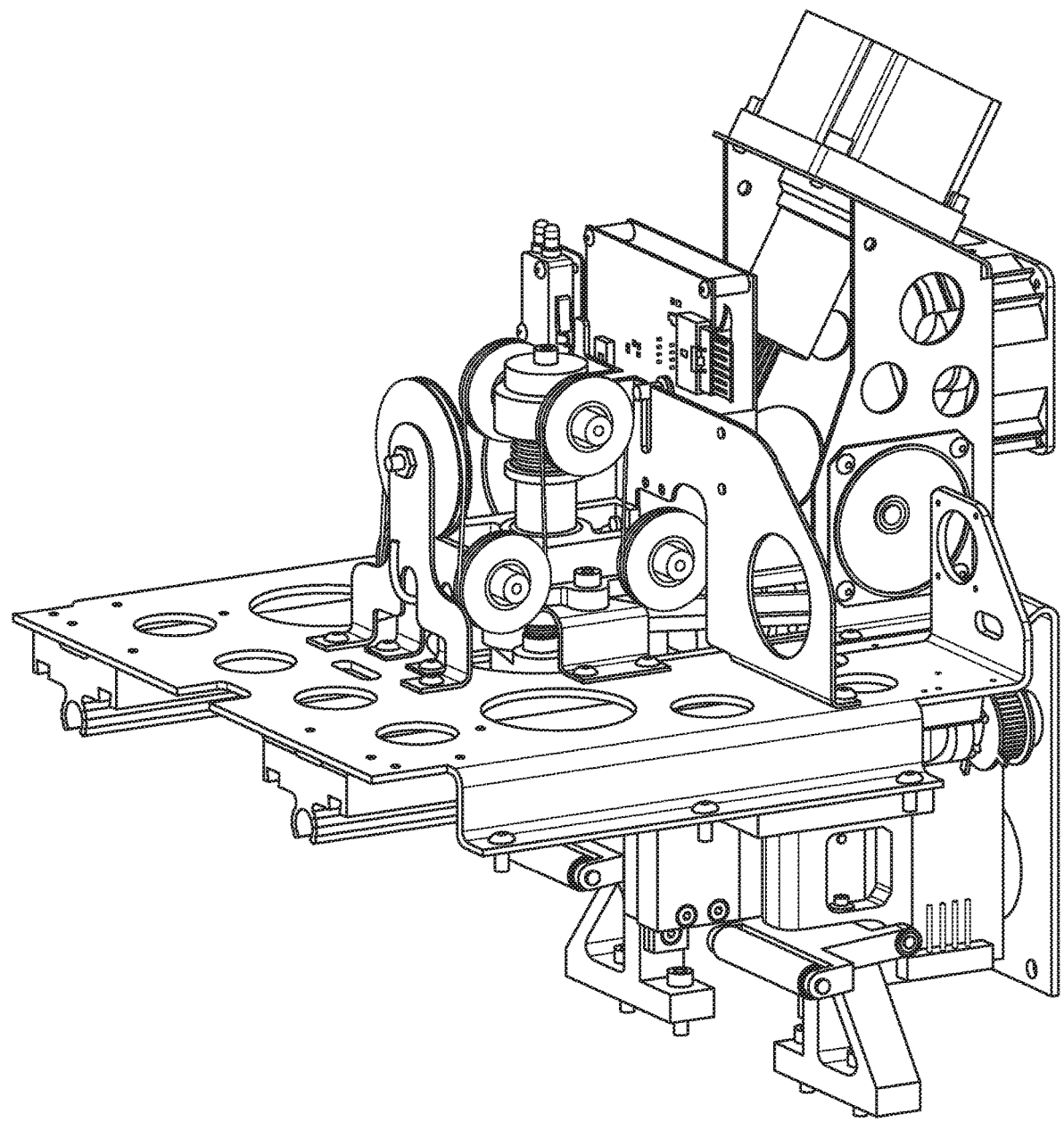
Figure 6B:
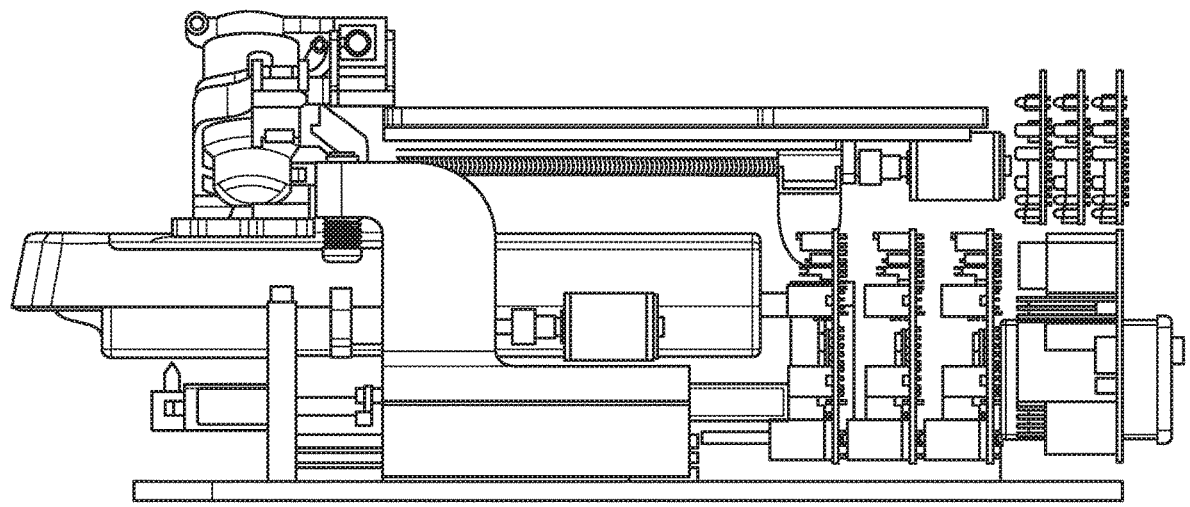
Figure 6B:
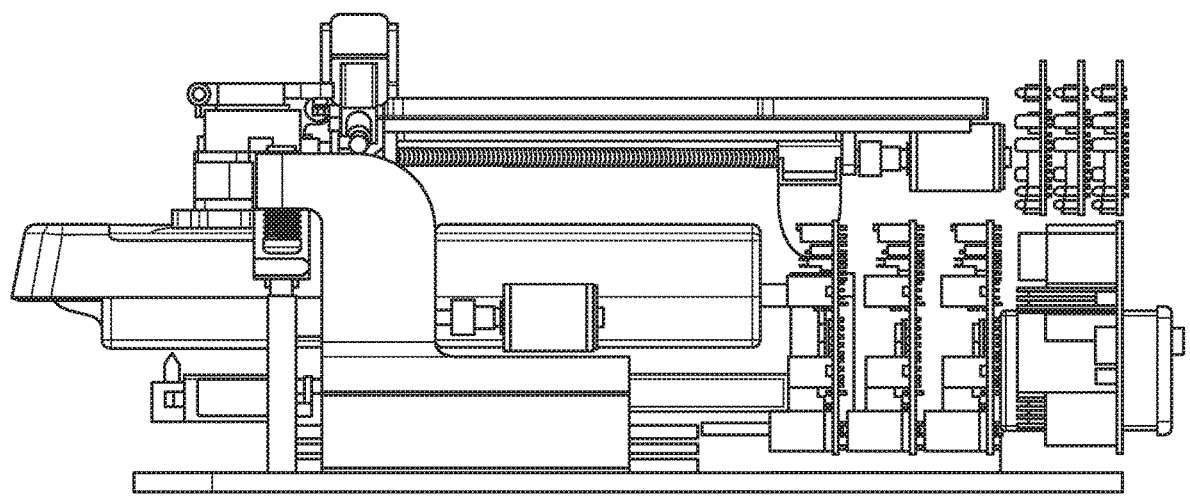

Those skilled in the art will appreciate that the invention described herein is adaptable to variations and modifications other than those specifically described. It is to be understood that the invention includes all such variation and modifications. The invention also includes all of the steps, features, compositions and compounds referred to or indicated in the specification, individually or collectively and any and all combinations or any two or more of the steps or features.

The present invention is not to be limited in scope by the specific embodiments described herein, which are intended for the purpose of exemplification only. Functionally equivalent products, compositions and where appropriate methods are clearly within the scope of the invention as described herein.

Throughout this specification and the claims that follow, unless the context requires otherwise, the word "comprise", or variations such as "comprises" or "comprising", will be understood to imply the inclusion of a stated integer or group of integers but not the exclusion of any other integer or group of integers.

Having regard to the above, this invention provides a unique method and device suitable for producing a cellular suspension of living tissue suitable for application to a patient in an epithelium-related procedure. In applying the method and/or in using the device, a donor tissue (e.g., skin epithelium such as glabrous epithelium, respiratory epithelium, vascular epithelium, corneal epithelium, and glandular epithelium) is harvested from a patient and subjected to a tissue dissociating means, and cells suitable for applying back to a recipient site of the same patient are collected. In some embodiments, the cells so collected can be cultured and expanded in vitro before applying to a recipient site. The cells can also be seeded to a scaffold or matrix where the cells can grow and/or proliferate into an artificial tissue or organ.

The cells may be presented in the form of a cell suspension (used interchangeably with "cellular suspension" herein) in a solution that is suitable for immediate dispersion (e.g., immediately after harvesting and/or filtering without in vitro culturing of the cells) over the recipient site. The cell suspension can be dispersed (immediately after harvesting or after in vitro culturing) to the recipient site alone or in combination with additional factor(s) such as heat shock protein(s), hyaluronic acid, platelet-enriched plasma, growth factor(s), and/or adipose stem cells, to facilitate, for example, wound healing, skin re-surfacing, or other epithelial treatments. The cell suspension can be dispersed via spraying, dripping, or any other application process. The cell suspension can also be injected directly into a tissue.

Aspects of the present invention include a system for cell harvesting and transplant, which can include: a cartridge for processing a tissue, comprising a tissue processing chamber, a disintegrator situated therein and a cell collection chamber separated from the tissue processing chamber by the disintegrator, wherein after dissociating the tissue placed in the tissue processing chamber mechanically and/or chemically and passing the dissociated tissue through the disintegrator, a cell suspension is collected in the cell collection chamber; and a programmable console for housing the cartridge and for providing motive power to supply a mechanical force and/or a chemical reagent to the tissue, wherein the console comprises a processor for controlling the console to supply the mechanical force and/or chemical reagent.

In some embodiments, the system of the present invention can be ReCell Next Generation (NG) product system. The system can include a re-usable Console, a disposable Cartridge (used herein interchangeably with "cassette") and optionally, a disposable Applicator. The applicator may reside in the cartridge until use. The cartridge with applicator can be a sterile packaged disposable. The cartridge carries the tissue processing chamber and the required materials (fluids and or solids) to treat and process the skin sample. The cartridge and applicator are passive devices which are acted upon mechanically by the console (after the cartridge is inserted into it) to achieve the required mechanical tissue working and fluid movements. All power sources and controls can reside in the console.

In some embodiments, the basic functions of the process are to 1) pre-treat the skin sample by soaking in heated enzyme, 2) rinse it with buffer, 3) mechanically grind it while submerged in additional buffer solution to disassociate the required cells, 4) suspend the cells in buffer, then 5) to convey the product suspension to the applicator so that the applicator can be used manually by an operator to apply the cell suspension to the patient's prepared wound bed.

Tissue processing may be accomplished by a number of methods or combination of methods. In the embodiment described herein, the grinding process involves exerting a compression and/or rotational force on the skin sample through a specially designed member ("Pestle Surface") while applying a partial rotational motion to the member. The fluid handling process involves automatic reconstitution of an enzyme powder with sterile water before introduction of the enzyme solution to the processing chamber, then removal of the enzyme to a waste container followed by one or multiple introductions of buffer or other solution to the chamber during the remainder of the process. Finally, the product fluid, a suspension of skin cells, is pumped to an applicator or other vessel or matrix for introduction to a wound.

Below is a description of the ReCell® NG, one possible embodiment of the invention. The system is designed, developed and manufactured in order to provide users a new and improved, automated, safe, efficient, predictable, reliable, and easy-to-use device for the treatment of areas larger than the manual ReCell kit (FIG. 1, described in detail below).

Some advantages of the automated systems include:
Minimize the time to process
Eliminate manual process steps, minimize user interaction and provide an automated process
At the end of the process, provide the cell suspension to the user in a vessel or applicator, the exterior of which remains sterile
Improve applicator and nozzle application for more intuitive use
Provide users with confidence in the consistency of suspension Further features of the present invention are described below. It is to be understood, however, that these examples are included solely for the purposes of exemplifying the present invention. It should not be understood in any way as a restriction on the broad description of the invention as set out above.

The following description is put forth so as to provide those of ordinary skill in the art with an exemplary description of how the compositions and/or methods claimed herein are made and evaluated, and are intended to be purely exemplary of the invention and are not intended to limit the scope of what the inventors regard as their invention. Modifications and variations of various aspects of the following examples will be apparent to those skilled in the art and are included within the scope of the present invention. For example, while some examples are described in connection with a skin-related procedure, the same can be applied to non-skin epithelial tissues (such as respiratory epithelium, vascular epithelium, glandular epithelium, corneal epithelium, and the like) with slight modifications that are well within the level of ordinary skills in the art.

Below are some exemplary designs of the system and various components therein.

1. Overview

The ReCell NG system is an autologous cell harvesting and transplant system used to treat a variety of skin or other epithelium-related conditions by application of a liquid suspension of harvested cells to the treatment area. This cell suspension is prepared from a sample of the patient's own skin or other epithelial tissue in an automated, autologous process.

The process employs enzyme and/or mechanical action to dissociate cells from the tissue sample, and put them into suspension in a buffer solution.

The system includes a disposable Cartridge or Cassette (FIGS. 2A-3B, two different designs shown); a reusable Console (FIGS. 4A-6B, two different designs shown) into which the Cassette is inserted; and optionally, a disposable Applicator (FIGS. 7-9) which is housed in the Cassette until ready for use.

The Cassette can be provided sterile and contain the process materials and a chamber that holds the tissue sample. It is sealed against microbial penetration. The Applicator is filled with the cell suspension while housed in the Cassette during the process, and is then removed for use after the Cassette is removed from the Console. The Console provides some or all of the motive power and control. In addition to the console, the cartridge may also have a mechanism for providing motive power (e.g., heat) so as to supply a mechanical force and/or a chemical reagent to the tissue.

The Applicator is capable of dispensing, spraying or dripping the cell suspension therein onto a recipient site or a support. For example, the Applicator can either spray or drip the cell suspension fluid on the treatment area or allow application beneath a contact layer dressing already in place, at the option of the physician. As an alternative or in addition to the Applicator, the system can include a support for receiving the cell suspension, wherein the support, after receiving the cell suspension, is presented for transplant or culturing. The support may be a matrix, a scaffold, a dressing, or any combination thereof; the support may be solid, semi-solid, porous or fragmented.

2. Manual ReCell

The ReCell NG system is an at least partially automated version of the previously developed ReCell manual process.

The manual process employs a ReCell Kit (FIG. 1) which is delivered with sterile and non-sterile components. The ReCell Kit contains one vial each of Sterile Water, lyophilized enzyme (powder) and compound sodium lactate buffer ("Buffer"). The enzyme is reconstituted by introducing 10 ml of sterile water in the enzyme vial. The enzyme solution is then placed in a heated well in the kit to bring the solution to 37 degrees C. The skin sample is then placed into the heated enzyme for a period of time to break down extracellular matrix and reduce the attachment between the epidermal and dermal layer. Buffer is taken from its vial and placed in a rinsing well in the ReCell processing unit. The required amount of Buffer to create the cell suspension is drawn into a 5 ml syringe. Increasing amounts of cell suspension volume allow treatment of larger surface areas. The skin sample can be a split-thickness biopsy (includes Epidermis, the dermal-epidermal junction and some Dermis) obtained by use of a dermatome or other similar standard device. Biopsies of 1-4 square cm may be used to create, for example, 1-4 ml of cell suspension. The cell suspension can be diluted or concentrated to increase or reduce its volume, as needed.

Once the skin sample has completed treatment in the enzyme, it is rinsed in buffer by dipping in the rinsing well. The sample is then set out on the kit "tray", epidermal side up. A scalpel is used to manually scrape off the epidermal and junction cell layers, to collect the cells in a small pool of buffer solution. While scraping, the sample is moistened with drops of Buffer solution to carry off the disaggregated cells into suspension. The correct total amount of Buffer solution is used in order to create the desired cell suspension volume.

The tray is manually tilted to move the cell suspension into a corner, from where it is drawn off with a syringe. The cell suspension is aspirated several times to rinse the tray and collect the maximum number of cells. The cell suspension is then dispensed from the syringe into a cell strainer basket (e.g., 40, 80, 100 or 200 micron size mesh, or any other size depending on the desired filtering application) sitting in a third well in the ReCell processing unit. The strainer is removed and the filtered cell suspension is then aspirated and drawn from the well with a new, sterile syringe. A spray head is then fitted to this syringe, thus creating an applicator which is used to spray or drip the cell suspension onto the treatment area. Alternately, a blunt needle is used to introduce suspension beneath a dressing.

3. ReCell System

The ReCell NG automated process includes three subsystems: Fluid Handling (optional), Tissue Processing and Application.

The Fluid Handling and Tissue Processing Systems have components that enclose and contact the tissue sample and fluids within the Cassette. These components form a sealed system. Magnetic and/or mechanical components of the Console exert forces on components of the sealed system, causing movements within the sealed system without mechanically breaching the system seal. This achieves the mechanical working of the tissue sample and fluid movements, while maintaining a microbial barrier.

The system is sealed against microbes. The Tissue Processing chamber may be vented with a "Tortuous Path" vent or anti-microbial filter within the system to allow air to leave and to enter without carrying microbes into the system. This is necessary to accommodate volume and pressure changes as the fluid moves through the system.

The basic mechanical working of the tissue sample can be achieved using a disintegrating member. In various embodiments, the disintegrating member may be part of the console (e.g., connected to the actuating mechanism) or part of the cartridge (e.g., situated in the tissue processing chamber and, e.g., connected to the cap). The disintegrating member can be a pestle or grinder.

Figure 13:
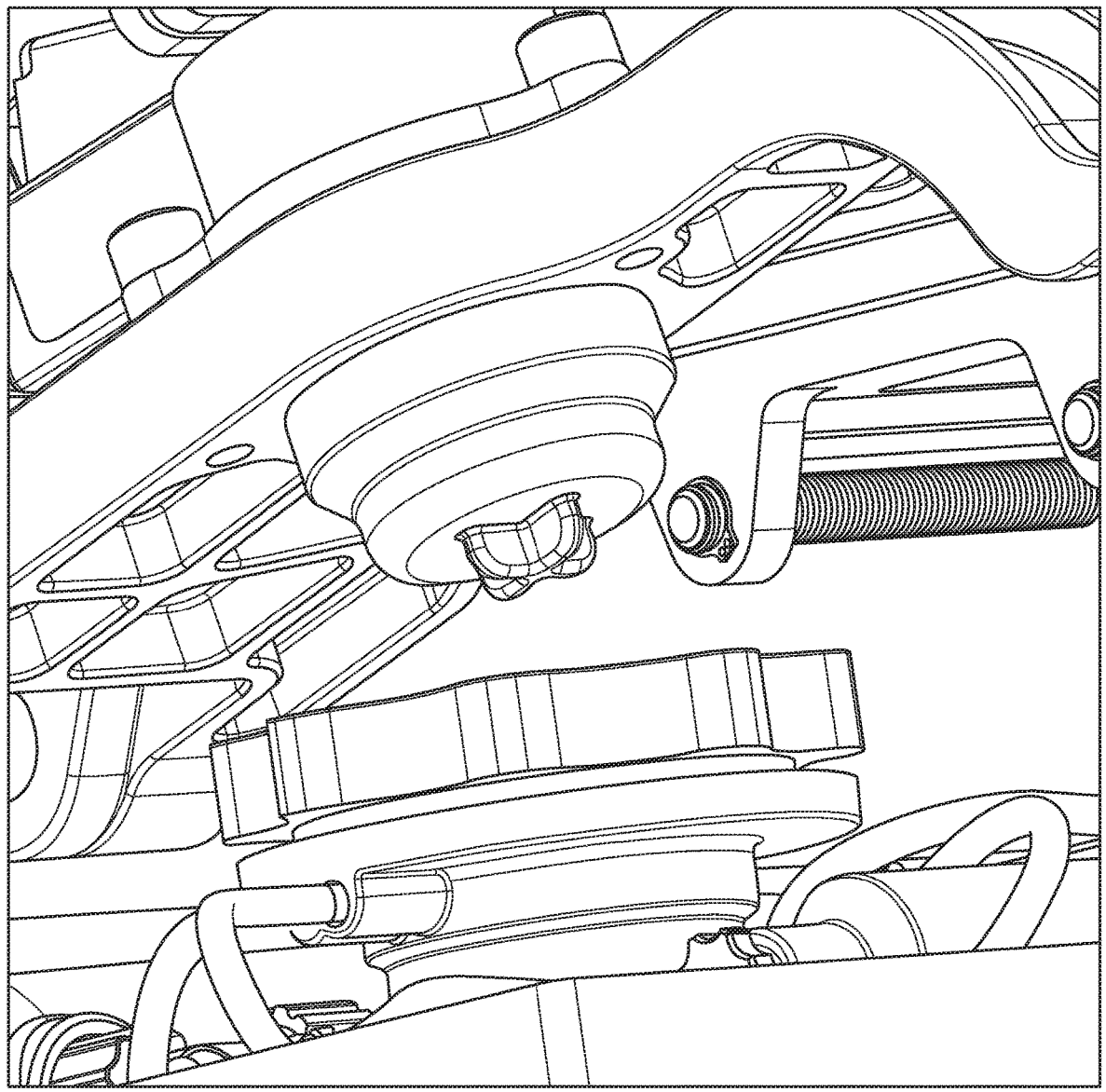
FIGS. 13-14 illustrate the "Pestle".
Figure 14:
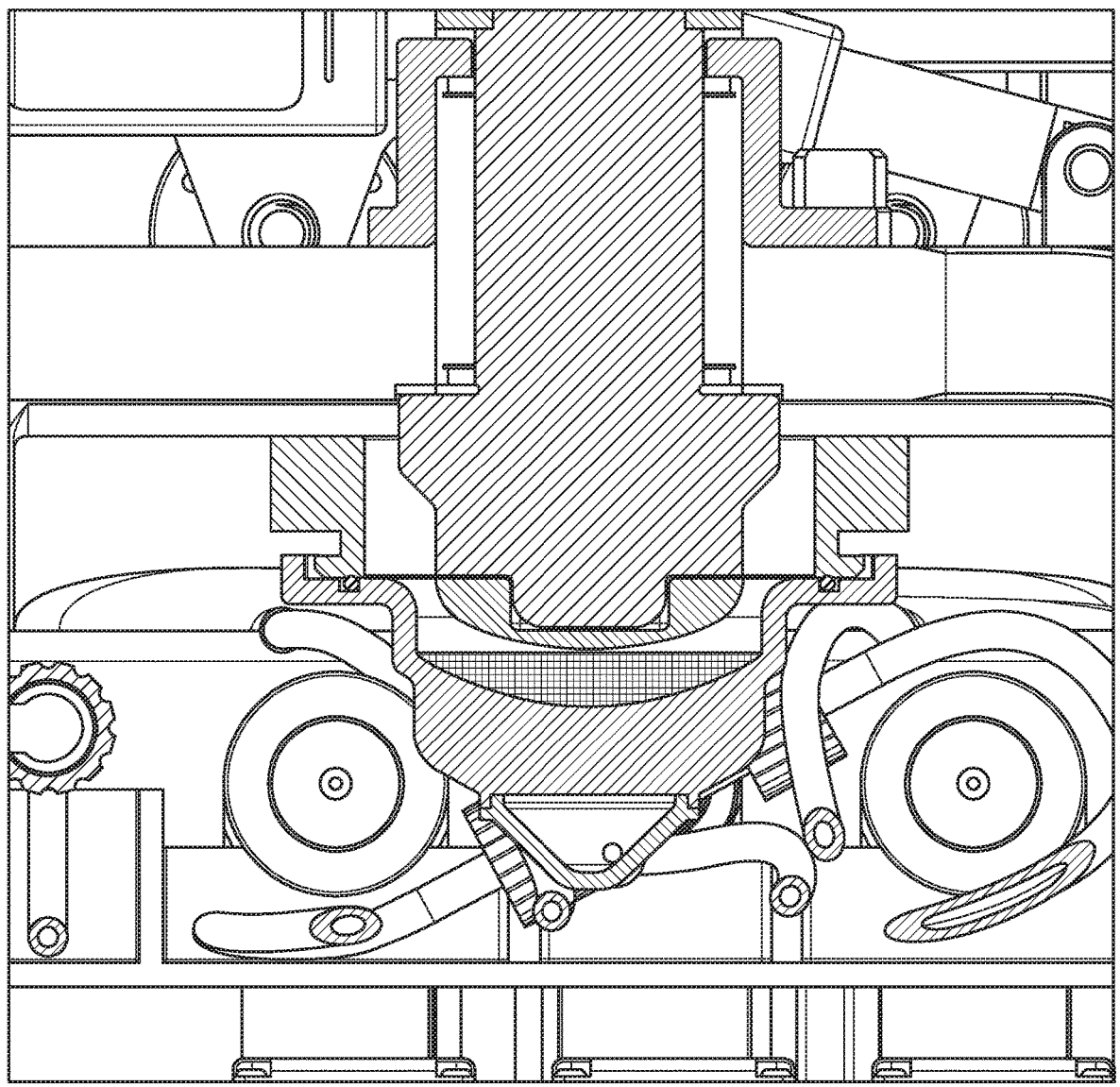

In one exemplary system, mechanical working is achieved by a reciprocating—rotating member, the "Pestle" (FIGS. 13-14), which applies linear and torsional force, and repeated impact to the tissue sample through a flexible seal. (The actuating portion of the Pestle ("Pestle Actuator Cylinder") is part of the Console and does not touch the tissue sample. The tissue sample is worked by a component mounted to the inside of a flexible seal ("Pestle Surface") through which force is transmitted from the actuating member in the Console. These forces are applied against the tissue as it sits on a coarse metal mesh or any suitable tissue disintegrator (e.g., a sheet with holes, blade, grid, screen, etc.), which helps concentrate the force and allow liquid and cells to drop therethrough. The Pestle Surface may have multiple radial ridges to also help concentrate forces, mimicking the action of the scalpel used in the current ReCell kit as the Pestle rotates. The number of ridges, their shape and the motion, force and time required to effect disaggregation can be adjusted and optimized. Other disintegrating member such as a grinder can also be used.

Alternative to or in combination with a pestle motion, mechanical working can be achieved by vigorously agitating the tissue sample which is placed in a bath of buffer (e.g., a compound sodium lactate buffer). For example, the tissue sample may be placed in a bath of buffer together with a sterile magnetic stirrer in the Cassette. The Console can provide a magnetic force to drive movement (e.g., rotation) of the magnetic stirrer, thereby physically disrupting the cellular stratum and disassociating the cells.

An outer surface of the Applicator can be sealed in a sterile packaging before transport to a sterile field for cell transplant. For example, the Applicator can be housed in a compartment in the Cassette, which is sealed with a peel-off film or any other sterile packaging, such that the exterior of the Applicator is maintained within a microbial barrier. The applicator can be a part of the system or a stand-alone device. The Applicator may be pressurized or spring-loaded. The Applicator may have a pivoting head for axial application of the cell suspension. The Applicator can be filled with cell suspension through a sealed path from the Fluid Handling System during the process, so that the cell suspension is not exposed until it is sprayed on the treatment area by the physician in the sterile field.

As an alternative or in addition to the Applicator, the system can include a support for receiving the cell suspension, wherein the support, after receiving the cell suspension, is presented for transplant or culturing. The support may be a matrix, a scaffold, a dressing, or any combination thereof; the support may be solid, semi-solid, porous or fragmented.

4. Fluid Handling System

Figure 15A:
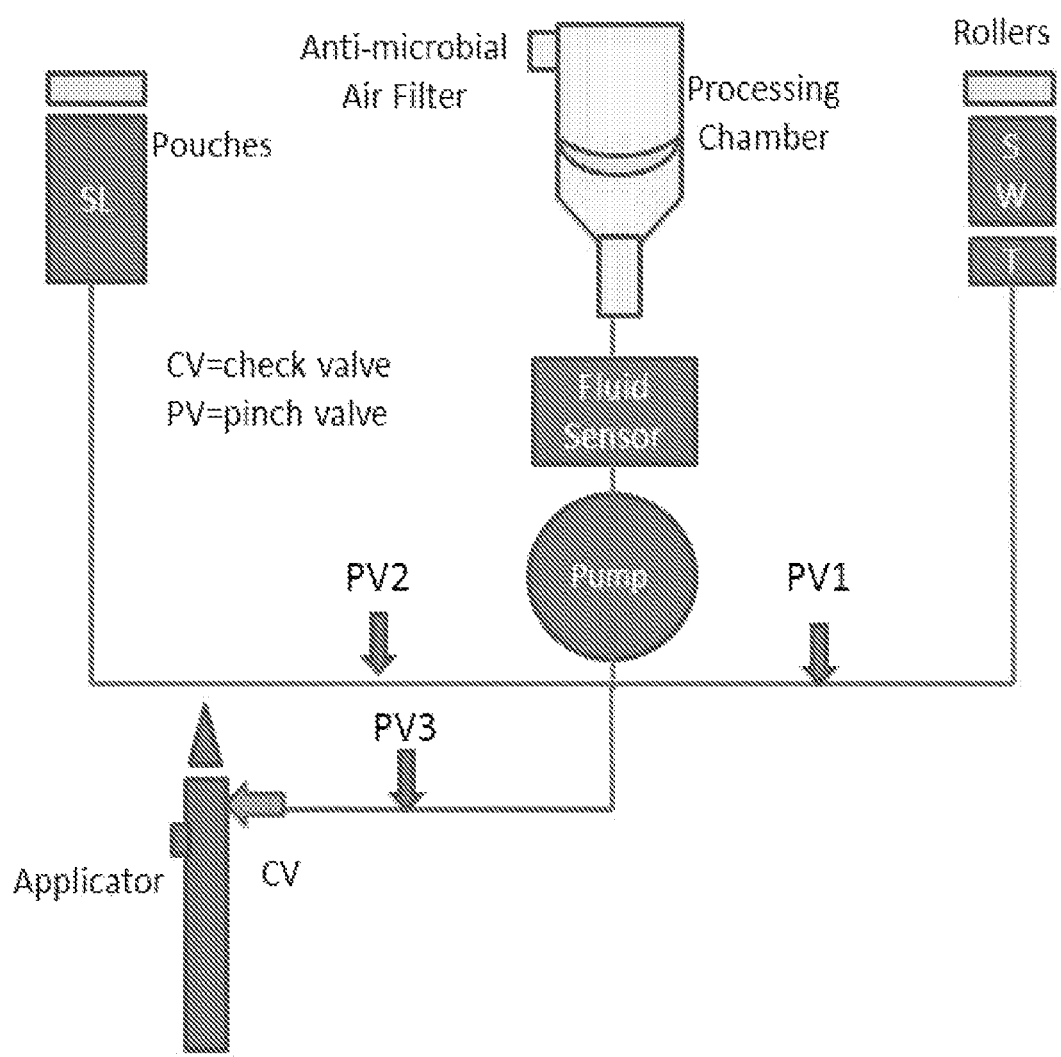
FIGS. 15A-15C illustrate an exemplary Fluid Handling System.
Figure 15B:
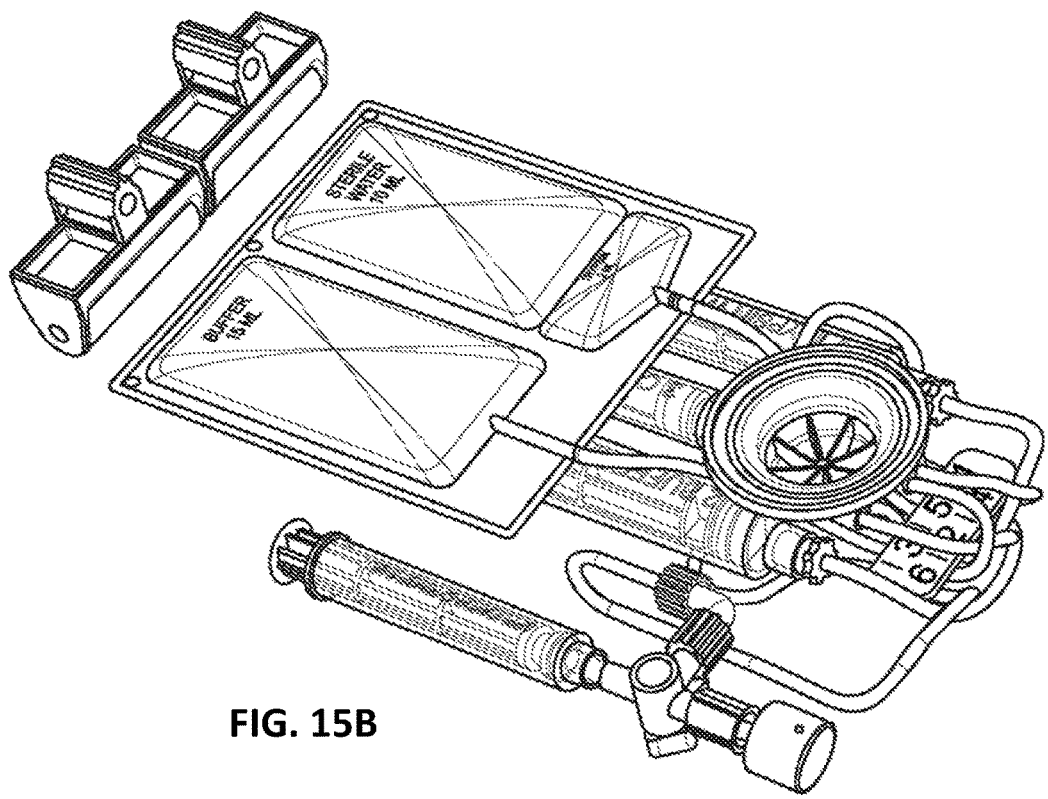
Figure 15C:
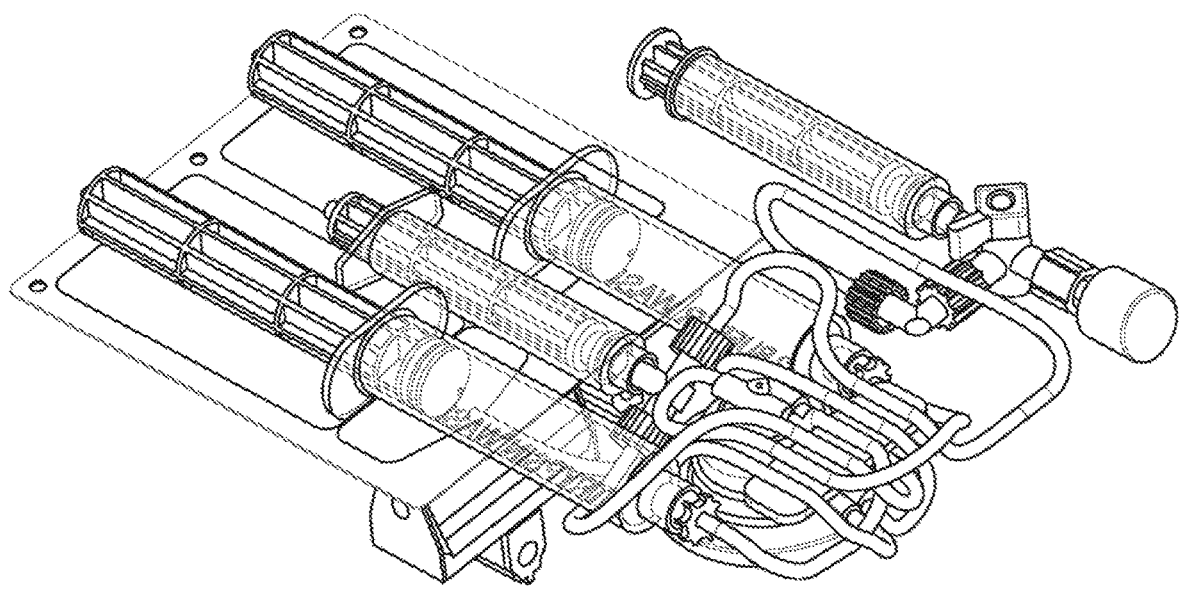

The Fluid Handling System is optional. For example, if the tissue sample has been partially processed (e.g., incubated with an enzyme such as trypsin solution and washed and placed in a buffer) before being placed in the Cassette, the Fluid Handling System can be eliminated. An exemplary Fluid Handling System is shown in FIGS. 15A-15C. FIG. 15A is a schematic of its operation. FIGS. 15B and 15C are exemplary hardware in the Cartridge handling the fluids. This includes the following items, which are part of the Cassette unless otherwise noted.

In various embodiments, the cartridge comprises a first packet for providing an enzyme solution and a second packet for providing a buffer solution, both packets in fluid communication with the tissue processing chamber, wherein the enzyme solution breaks down extracellular matrix in the tissue thereby chemically dissociating the tissue, and wherein the buffer solution washes the dissociated tissue and suspends cells in the cell suspension. For example, the first packet can have a first and a second container separated by a breakable seal, the first container containing sterile water and the second container containing lyophilized enzyme powder, wherein when the seal is broken, the lyophilized enzyme powder meets the sterile water and dissolves therein. Such first or second container can be a pouch, a vial or a syringe. To deliver the reagents to the tissue, the console can further comprise a first pressurizing mechanism for driving the enzyme solution and a second pressurizing mechanism for driving the buffer solution out of the first packet and the second packet, respectively, into the tissue processing chamber. In some embodiments, the first packet further collects waste enzyme solution after use and the second packet further collects waste buffer solution after use. The first packet can be in fluid communication with a first pump for pumping the enzyme solution and the waste enzyme solution. The second packet can also be in fluid communication with a second pump for pumping the buffer solution and the waste buffer solution. In some embodiments, the cartridge further comprises a pump for drawing the cell suspension from the cell collection chamber, and subsequently after filled, pumping the cell suspension into the applicator, the third pump in fluid communication with the cell collection chamber and the applicator. Two or all of the first, second and third pumps can be the same pump. The first, second or third pump may be peristaltic, syringe, or other type of pump and may be disposable or reusable. In some embodiments, the cartridge further comprises a first syringe for collecting waste enzyme solution and a second syringe for collecting waste buffer solution, both syringes in fluid communication with the cell collection chamber. The cartridge can also further comprise a third syringe for drawing the cell suspension from the cell collection chamber, and subsequently after filled, pumping the cell suspension into the applicator, the third syringe in fluid communication with the cell collection chamber and the applicator. In certain embodiments, the cartridge further comprises a fluid detector for controlled metering of the enzyme solution and the buffer solution. As an alternative to the pouches, the cartridge can include three containers for providing an enzyme solution, sterile water and lyophilized enzyme powder, respectively.

An exemplary Fluid Handling System includes:
Two sealed packets which hold the fluids and enzyme powder (for chemically dissociating the tissue, which can include, for example, digestion with enzymes such as trypsin, dispase, collagenase, trypsin-EDTA, thermolysin, pronase, hyaluronidase, elastase, papain and pancreatin). Packet 1 has two chambers separated by a seal. The first chamber holds Sterile Water and the second holds lyophilized Enzyme powder. Packet 2 holds sodium lactate Buffer, or other solution to make up the cell suspension. Alternatively, three containers can be used for providing an enzyme solution, sterile water and lyophilized enzyme powder, respectively. The water and enzyme can be stored in separate containers connected by tubing or other means.

Two Rollers (or other suitable pressurizing mechanism such as pressure plates) (part of the Console), being used to drive the fluids out of the packets.

Two fluid paths connecting the two packets to the Tissue Processing Chamber.

The Tissue Processing Chamber (also part of the Tissue Processing System).

The Cell Collection Chamber below the Tissue Processing Chamber.

A common fluid path comprising tubing that interfaces with a pump and fluid/air detector, for metering and moving the separate fluids.

A fluid path to fill the Applicator.

A set of pinch valves (or other valves such as rotary, piston, sliding gate valves; part of Console) which rise and fall to close or open each of the fluid paths when required in the process cycle.

The Applicator (optional), which remains an integral part of the Fluid Handling System until it is removed from the Cassette for use by the physician in the sterile field.

In various embodiments, the cartridge may further comprise at least one supplying container for providing an exogenous agent. For example, the exogenous agent can be a heat shock protein or a fragment thereof, hyaluronic acid, platelet-enriched plasma, a growth factor, adipose stem cells, or any combination of the foregoing.

Where desirable or required, one or more components of the cartridge or the fluid handling system in contact with a biological material is removably assembled therein so that such component can be removed from the cartridge for biohazard disposal allowing the rest of the cartridge to be recycled.

Where a pump is needed, the pump can be peristaltic, syringe, or other type of pump and may be disposable or reusable. The pump can be part of the console and be reusable, or can be part of the cassette and be disposable. For example, a peristaltic pump motor and actuators can be incorporated into the durable console and interface with a length of tubing. The peristaltic pump motor can have rollers attached to it in either a rotary or linear configuration. These rollers can contact the tubing, squeezing the tubing to occlude it and drive fluid along the tubing path.

A disposable pump (e.g., peristaltic pump) can be advantageous as a complete, simple, inexpensive pump that is entirely enclosed within the consumable cassette part of the system. The disposable pump can mate via a simple, physical interface to a motor that is part of the durable console. An exemplary disposable pump is Quantex Pump available from Quantex Arc Ltd (London, UK).

5. Fluid Handling Process

This is optional depending on whether the tissue sample has been processed or partially processed or not before being placed in the Cassette. Fluid handling can be omitted if the tissue sample has been at least partially processed before entering in the Cassette. Partial processing, in one example, includes incubating the tissue sample with an enzyme such as trypsin solution and washing and placing it in a buffer before placing the tissue sample in the Cassette.

Where fluid handling is needed, all Valves close upon insertion of Cassette in Console. First Roller ("Enzyme Roller") pushes forward, compressing the sterile water and breaking the seal with the enzyme powder pack. This joins the two chambers into one.

First Roller stops to give Enzyme a delay period to dissolve in water Roller could either have a set percentage advance before pausing or be controlled by a pressure switch.

A First Valve opens (on "Enzyme Feed Tube"). First Roller then continues to advance, breaking second seal between the combined Sterile Water/Enzyme packet and the "Enzyme Feed Tube" which leads to the Tissue Processing Chamber.

First Roller resumes advancing to move enzyme solution out of the packet. A peristaltic pump (or any other pump) moves the solution into the combined Tissue Processing Chamber and Cell Collection chamber to fill it and cover the tissue. First Valve closes. A variable/settable delay while tissue sample soaks in Enzyme solution. (Note: Temperature can be maintained with a sensor and coil in the wall of the Tissue Processing Chamber or through a thermal pin extending up from the Console. During this period, Pestle may cycle up and down to help agitate Enzyme solution and promote tissue treatment. This may allow shorter soak period. Other means to move the fluid employed can also be used, such as rotating the pestle, with or without adding fins, and pumping small amounts of the solution in and out of the chamber.)

The First Valve reopens and the peristaltic pump (or any other pump) draws Enzyme solution out of the combined Tissue Processing & Cell Collection Chamber through the Enzyme Drain Tube and stores it in packet #1 (the now empty enzyme pouch) for storage as waste. The First Valve closes. A Second Valve opens (on "Buffer Feed Tube"). Second Roller ("Buffer Roller") advances partially, breaking seal. The peristaltic pump (or any other pump) both meters the volume and pumps Buffer solution through Buffer Feed Tube to rinse the tissue sample in the Tissue Processing Chamber. (Buffer may enter through multiple ports for surface coverage.) Sufficient Buffer is pumped in to completely fill the Tissue Processing/Cell Collection chamber combination. The Valve then closes.

The First Valve opens again. The peristaltic pump (or any other pump) draws all rinse Buffer out of the processing chamber and into packet #1 for storage as waste.

The volume of the Cell Collection Chamber can be adjusted for the tissue sample size and Buffer volume to be used.

The disaggregation process then begins (See Tissue Processing Section below). The Second Valve opens, the Second Roller continues to advance, and the peristaltic pump (or any other pump) moves Buffer solution into the chamber once or several times during the Pestle movements to repeatedly douse the tissue sample with drops of Buffer solution, pausing in between in a fashion coordinated with the movements of the Pestle. The Valve closes between aliquots. (Note: The Buffer packet may be designed with stepped width to increase volumetric accuracy in the small volume applications. The Roller can be controlled with a flow control meter.

Figure 10:
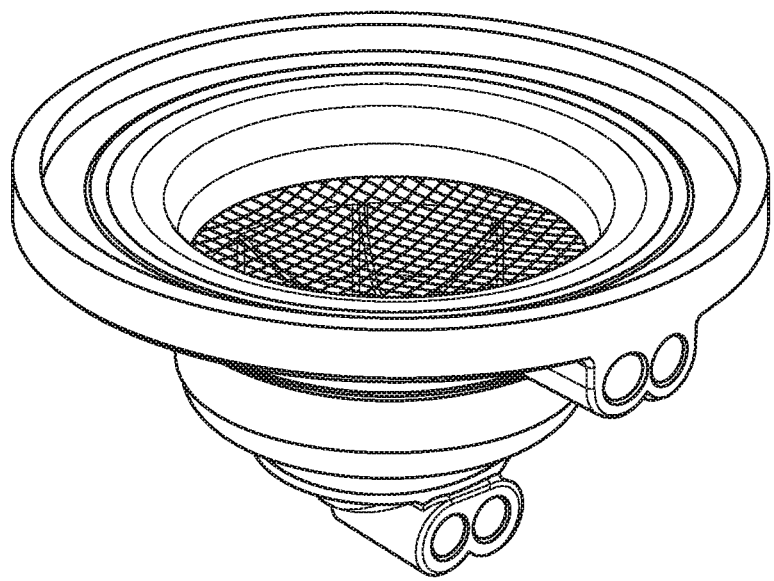
FIGS. 10-12 illustrate Tissue Processing and Cell Collection Chambers.
Figure 11:
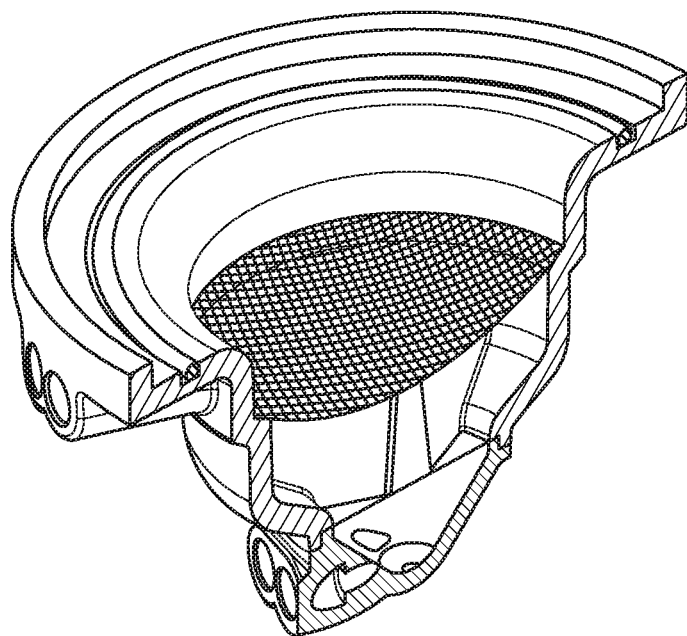
Figure 12:
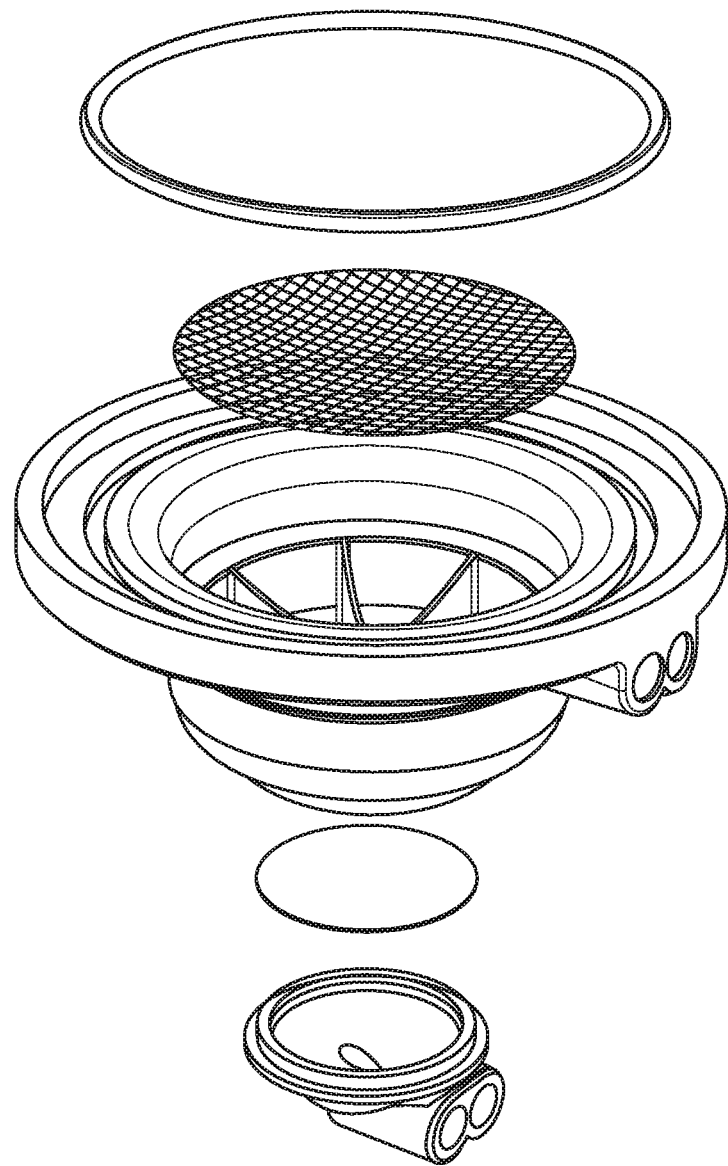

During this process the Buffer picks up the cells being liberated from the tissue sample, and the Cell Suspension thus created drains by gravity into the Cell Collection chamber, passing through the 100 micron filter (or 40, 80, 150 or 200 micron size mesh, or any other size depending on the desired filtering application) mounted in the Cell Collection chamber. (See Section on Tissue Processing and FIGS. 10-12 on the Tissue Processing and Cell Collection Chamber Assembly.) At the end of the Pestle Cycle, additional Buffer is added to the chamber to rinse it and collect all the disaggregated cells and to make up the volume of Cell Suspension needed. This may occur multiple times in order to completely capture all cells and achieve desired volume. The Second Valve then closes and remains closed.

After tissue processing is complete, a Valve opens (on "Cell Collection Tube"). The pump draws Cell Suspension out of Collection Chamber (through a filter) and into the applicator. The pump then reverses and pumps the Cell Suspension abruptly back into the Tissue Processing/Cell Collection chamber to wash cells off the Chamber and Pestle surfaces and further activate cells. This may be repeated. After this process the Suspension remains in the Applicator. The Valve then closes.

Additional Buffer may be drawn from the Buffer packet and pumped to the chamber (as described above) to rinse it and collect additional disaggregated cells and to make up the volume of Cell Suspension needed. This may occur multiple times in order to completely capture all cells and achieve desired volume. This additional suspension is pumped to the applicator and the pump then reverses and pumps the Cell Suspension abruptly back into the Tissue Processing/Cell Collection chamber to wash cells off the Chamber and Pestle surfaces and further activate cells.

6. Tissue Processing System

The Tissue Processing System is a combination of elements of the Cartridge and Console, shown in FIGS. 2A-3B (two different Cartridge Designs, #1 and #2), 4A-6B (two different Console Designs, #1 and #2), and 10-12 (Tissue Processing and Cell Collection Chambers).

Tissue Processing Chamber: A vessel constructed of engineering resin (or any other suitable materials) with a steel mesh (or any other suitable disintegrator) over an opening at the bottom ("Tissue Processing Mesh"), supported by a strong rib structure or circumferentially. The top of the chamber is closed with a cap ("Chamber Cap"). One combined port or two separate ports in this chamber allow Enzyme Solution and Buffer Solution to be pumped in. (Buffer may enter through one or two or multiple ports for surface coverage.)

Chamber Cap: A cap removably placed on or hinged to the Tissue Processing Chamber can be used to seal the top opening thereof, e.g., through a bayonet fitting. Once closed, the cap can be locked in place by a locking mechanism, such that the cap remains closed during processing and cannot be reopened or reused after first use. The body of the cap includes a flexible elastomer (e.g., polyurethane) seal, with a raised Pestle surface (spherical convex) fastened on the chamber side of the Cap, and a spline indentation on top. When the cap is fastened to the chamber, a tortuous path vent at the O-ring seal or elsewhere (or alternatively, an anti-microbial filter) allows air to pass, but seals against microbe intrusion. The Cap can also be substantially rigid with a form of vertical axil with o-ring or quad-seals or other sealing device.

Tissue Processing Mesh: A stainless steel mesh with a concave spherical shape, covering an opening at the bottom of the Tissue Processing Chamber, separating it from the Cell Collection Chamber below. When the tissue sample is placed in the processing chamber it sits on the Tissue Processing Mesh. Any suitable tissue disintegrator (e.g., a sheet with holes, blade, grid, screen, etc.) can also be used.

Cell Collection Chamber: A chamber beneath the Tissue Processing Chamber, with a filter (e.g., 100 micron, 200 micron, or larger or smaller) mounted such that the Cell Suspension draining from the Tissue Processing Chamber passes through it before passing into the bottom of the Cell Collection Chamber to remove or collect large aggregates or tissue pieces. In certain embodiments, the cartridge further comprises a filter situated between the disintegrator and the cell collection chamber, for filtering the processed tissue to remove large aggregates. A filter can be alternatively or additionally situated between the cell collection chamber and the applicator, for filtering the cell suspension to remove large aggregates. (Note: The volume of the Cell Collection Chamber may be variable to allow for various low volumes of Buffer solution to be used, while maintaining coverage of the tissue sample with Buffer by the end of tissue processing.)

Actuating Mechanism (Console component): A member that allows forces to be passed through the cap to the tissue sample. The Actuating Mechanism will have a key that allows mating with the Chamber Cap to allow disaggregation. When the pivot arm is in the retracted position (FIGS. 5B upper panel, FIG. 6B upper panel and FIG. 13), a cylindrical disintegrating member (Console component) is pulled clear of the cap such that it does not interfere with the Cassette being moved in and out of the Console; when the pivot arm is in place (FIG. 5B lower panel, FIG. 6B lower panel and FIG. 14), the bottom of the disintegrating member is placed upon a seal or membrane within the Cap. For example, the seal on a first side facing the tissue processing chamber can have a working surface, wherein when the disintegrating member is actuated and placed upon a second side of the seal facing the disintegrating member, the working surface is in contact with the tissue placed in the tissue processing chamber. Alternatively, the disintegrating member can be a part of the cartridge (e.g., connected to Chamber Cap or Tissue Processing Chamber), such that upon mating with Actuating Mechanism, the disintegrating member can be worked by the Actuating Mechanism to exert force to the tissue.

The Actuating Mechanism can be rotated in an oscillation through an arc. This allows application of torsion to the tissue sample.

Spring-loaded or mechanical, magnetic or other force on the Actuating Mechanism allows a steady force to be applied to the tissue sample, directly or through a membrane.

Cyclic lifting and dropping of the Actuating Mechanism allows impact or varying forces to be applied to the tissue sample.

All the applied forces discussed above are transmitted to the tissue sample directly (when the disintegrating member is a part of the Cartridge) or through the seal on the top of the Chamber Cap of the Cassette, without breaking the seal, so the microbial barrier around the tissue sample is maintained throughout the process.

An alternative or additional design to the above Chamber Cap and Actuating Mechanism module is to provide a magnetic stirrer in the Tissue Processing Chamber, and to drive the magnetic stirrer by a magnetic force provided by the Console. The magnetic stirrer, upon sufficiently vigorous stirring, breaks down the tissue sample into a plume of cells which can then be filtered and collected in the Cell Collection Chamber.

7. Tissue Processing

This process seeks to somewhat mimic the scraping action of the scalpel on the tray surface in the manual ReCell kit, with the added working elements of a metal mesh and impact from the Pestle. These additional working elements seek to provide enough action to disassociate the required cells regardless of the orientation of the sample.

After the Buffer rinse described above, the Actuating Mechanism moves toward the cap to mate with the keyed Chamber Cap surface and apply force (directly or to the Pestle Surface) against the tissue sample. (See FIG. 14.)

A mechanism to cyclically raise and drop and/or rotate the Actuating Mechanism at a proscribed frequency, can be applied to provide a cyclic impact or variable force of the Pestle Surface on the tissue sample.

A linkage mounted on the Actuating Mechanism provides the ability to rotate the Pestle actuator. With the multiple ridges on the Pestle Surface, an oscillating motion at this arc can sweep the ridges to cover the whole sample surface.

The above process continues for a prescribed number of cycles. When complete, some remnants of Dermis will be stuck in the mesh. The desired cells will be suspended in the Buffer in the Cell Collection Chamber.

Alternatively or in combination with the above Actuating Mechanism, the Console can provide a magnetic force which drives the movement of a magnetic stirrer previously placed in the Tissue Processing Chamber. The movement of a magnetic stirrer can break down the tissue sample into a plume of cells.

8. Applicator

Figure 7:
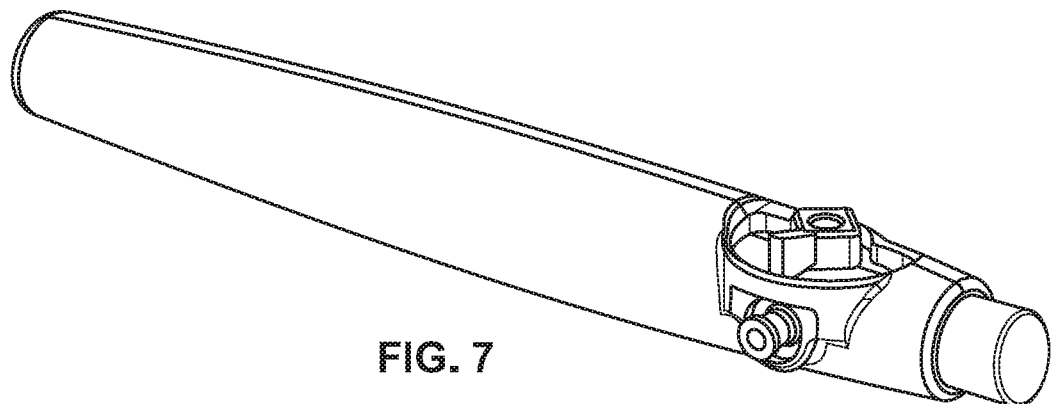
FIGS. 7-9 illustrate a disposable Applicator.
Figure 8:
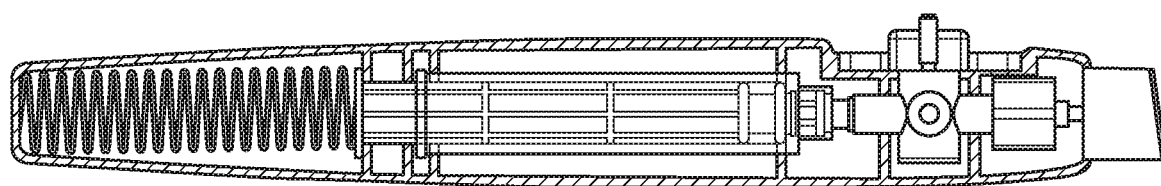
Figure 9:
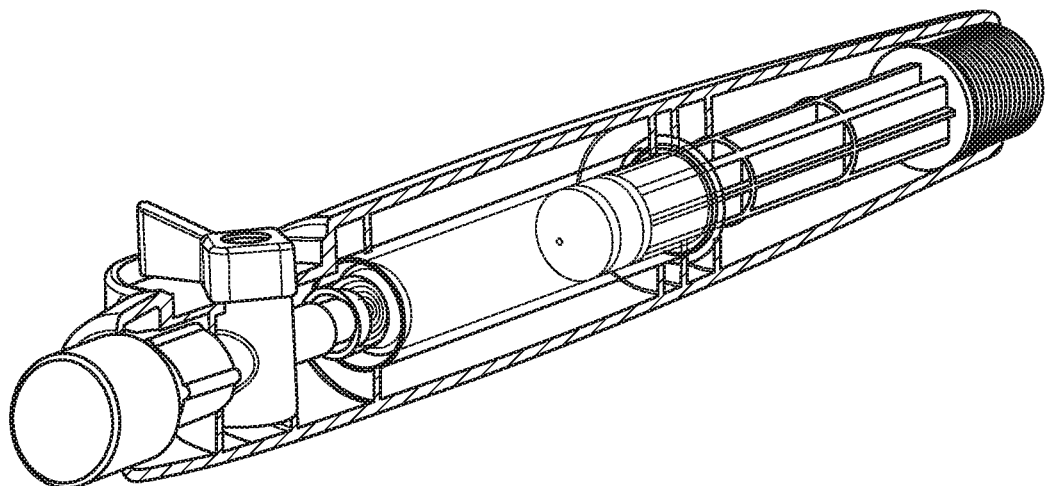

The design of the Applicator is shown in FIGS. 7-9.

The Applicator contains a spring-loaded syringe, with the spring oriented to resist filling of the syringe.

An operating valve on the Applicator is positioned and set to allow the Applicator Syringe to fill, but to stop the fluid from exiting the spray nozzle on the Applicator.

Alternatively, the applicator may include a septum or e.g., silicone rubber. This septum would be positioned adjacent to a fellow septum in the cartridge. When the cartridge is inserted into the console it mates with a boss that is stationary. This forces a spring loaded needle through both septa opening a fluid path from the cartridge plumbing to the applicator allowing it to be filled. When the cartridge is removed from the console, the spring loaded needle retracts resealing both septa and ensuring sterility.

The spring compression maintains pressure on the fluid while it is in the Applicator and as it is later emptied onto the treatment surface.

After the Applicator is filled, the Cassette is removed from the Console and the Cassette is carried to the Sterile Field, the circulating nurse opens the still sterile applicator chamber in the cartridge and presents it to the scrubbed-in nurse or physician, who aseptically retrieves it for application to the patient.

The physician points the Applicator nozzle at the treatment area and opens the operating valve partially or fully to achieve the strength of flow desired, from a drip to a spray. (The operating valve may be any suitable valve.) The applicator may have a pivoting head for axial application of the cell suspension.

As an alternative or in addition to the applicator, the system can include a support for receiving the cell suspension, wherein the support, after receiving the cell suspension, is presented for transplant or culturing. The support may be a matrix, a scaffold, a dressing, or any combination thereof; the support may be solid, semi-solid, porous or fragmented.

9. Console

The console internal layout is shown in FIGS. 5A-6B as two different designs (Console Design #1 and #2).

Some or all active, powered mechanical components and electrical components of the System reside in the console. (All Cassette components may be passive, mechanically driven by powered Console components, with the possible exception of a heating coil and sensor that may be placed in the Cassette.) The Console can have devices or means of recognizing that a Cassette is genuine and not previously used based on a passive signature device in the Cassette (authenticating, e.g., through a barcode or ID chip). Alternatively, the cartridge may also have some active components, such as a mechanism for providing motive power (e.g., heat) so as to supply a mechanical force and/or a chemical reagent to the tissue.

In some embodiments, the console further comprises one or more of: a mechanism for drawing and ejecting the cartridge into or out of the console; an interlock to prevent removal of the cartridge during processing; an operator interface to control processing time, suspension volume needed, and activation of tissue processing; a display panel showing status of tissue processing; and an ejecting mechanism for ejecting the applicator when filled.

In various embodiments, the system may include a custom control software for directing a processor or computer chip in the console to control the automated process. The system may also be connected to an external computer for collecting and processing data.

Mechanical Systems: The main mechanical systems are described above and summarized below:

Fluid Packet Rollers: These ride on lead screws driven by stepper motors, one motor for each roller.

Pump: Interfaces with tubing in the cartridge for fluid movement.

Actuating Mechanism: A mechanism for providing force and oscillation to the disintegrating member, and its rotation linkage.

Valve Actuation: The Valves which control opening and closing of all tubing are to be actuated by solenoids.

Control Electronics are also included to achieve the following:

Operation of the ReCell NG Instrument internal subsystems can be monitored and controlled by an electronic system including one or more microcontrollers interfaced to various actuators, sensors, and user interface components.

Additional resources for the microcontroller(s) may include flash memory, a real-time clock with battery back-up, and serial interfaces to external computers. Instructions for the microcontroller are contained in a firmware program loaded into flash memory, which allows for easy installation of updates/upgrades.

Actuators, such as motors, are turned on or off by the microcomputer via Digital Output (DO) circuits. Alternatively, power to the motor (and hence speed) can be varied using digital outputs controlled by timers and counters, which is a technique called Pulse Width Modulation (PWM).

Sensors may be used to measure or indicate important physical parameters, such as position of the roller mechanism, the force applied by a roller, or an internal temperature. Sensor outputs are read by the microcontroller using either analog-to-digital converter (ADC) or Digital Input (DI) circuits.

The user interface (e.g., backlit color LCD touchscreen, fixed touch screen, simple buttons or knobs or LEDs, etc.) includes means of data input, means for outputting various data to displays, indicators or audio generators. These types of devices may be purchased as a module that includes circuitry to operate the more complex components (e.g., touch switches or displays) and often communicate with the microcontroller via an internal bus.

A program executing on the microcomputer periodically scans the various inputs, such as the user interface switches, position sensors or a temperature sensor, and then determines the appropriate output actions, such as turning on or off a motor or heater. Software is discussed in detail below.

Operator Interface: An exemplary operator interface can be a control panel. The interface can also be a touchscreen. The following functions can be included:
- Able to visually determine key parameters from 3 meters distance and minimum 45° angle Progress (bar or other qualitative visual indicator as well as a countdown clock)
- Process complete and suspension ready indicator
- Fault or Error indicator
- AC Power indicator: lit when plugged in and power is available, regardless of whether the console is powered on or off.
- On/off switch
- Status indications
- Power on/off
- Processing and run status
- Standby
- Fault/Error
- User interface shall be readable in varying lighting conditions, including lighting conditions encountered in a typical Operating Room
- Count-down timer to be precise to within one minute
- Audible and Visual indicator of process completion and of fault/error
- Buttons, keys, or touchpad for user input with audible feedback
- Provide instructions or prompts for the user
- Allow user to input suspension volume desired
- Allow user to enter process level
- Instruments shall provide positive feedback that the cartridge is properly seated.
- Instrument must ensure that cartridge remains properly seated throughout the procedure, detect if cartridge is bumped or moved out of operating position, and provide fault condition notification
- The cartridge shall automatically align with the interface of the console
- The cartridge shall mate with the console in only one orientation
- Cell processing does not have to be visible by operator
- Inactivity—instrument shall automatically turn off:
  - After 120 minutes of inactivity (no button press, cassette insertion, etc.) after power on and before cycle started
  - 90 minutes after cassette removed at end of cycle
- Visual and audible advance notice of shutdown 15 minutes before
- Provide an override option
- Do not power down if cassette is not removed at end of cycle but provide visual and auditory reminder signal at 2 minute intervals
- Alarms:
  - Cartridge pack not seated properly
  - Over temperature at the mortar
  - Internal fault in processing
  - Power failure In various embodiments, the system may include a custom control software for directing a processor or computer chip in the console to control the automated process. The system may also be connected to an external computer for collecting and processing data.

Software:
Software can be written in C/C++ or other programming language. A real-time operating system or executable may be utilized to provide support for timing and resource management. Some functionality could be implemented using programmable hardware solutions such as FPGAs, or combination hardware/software devices such as "Programmable System on a Chip".

The processing architecture can be determined by the processing and timing requirements, power consumption constraints, etc. A multi-processor design may also be utilized to partition functionality (e.g., separate processors for display, touch screen, battery monitoring, consumable interface).

Development tools (e.g., cross compiler, HAG debug interface) for each processor can be utilized in the instrument. Open-source tools such as Git, CVS, Bugzilla etc. can be used for software configuration management and defect tracking.

Support software to perform instrument interface and debug functions can be included.

The following functions are included:
- Monitoring and control of the consumable interface:
  - Thermal control
  - Fluidic control, including pumping, positioning, pouch roller positioning, valve actuation, and necessary sensors (air, pressure, position, etc.)
  - Disaggregation control (control of pestle positioning and movement, necessary sensors, etc.)
  - Consumable detection (prevent absent or improperly seated consumables)
  - Consumable authentication (assure a genuine cassette and prevent reuse)
- User interface
  - Cell processing workflow
  - Hardware interface: graphical display, audio output, discrete status indicators and operator inputs
- Power
  - Monitoring AC power status
  - DC power status and control
  - Monitoring of battery status
  - Control of battery charging
  - Control of system electronics to implement power saving mode of operation
- Instrument self-test as determined through risk analysis and control (independent monitor processor or watchdog timer, POST, etc.)
  - Start-up self-test
  - In process self-monitoring to maintain essential performance
- Monitoring and control of a real-time clock for date/time
- Duplex Communications to an external computer through a wired interface (USB 2.0, RS-232)
- Logging of instrument operation in an event log
- Logging of detected alarms, faults, etc., in a service log
- Configuration of instrument operation (e.g., language selection)
- A debug/Software upgrade mechanism implemented thru a wired communications port (USB, RS232, JTAG, etc)

Power:

The electronic system can be powered by a battery or a universal supply capable of converting AC line voltage into several DC levels that will be required by the various circuits. The supply is universal meaning that it can accept the range of input line voltages and frequencies used by most countries. A separate power cord will be used in order to accommodate the different wall outlet configurations in different countries.

The power cord will plug into an entry module that includes a power switch and line filter that attenuates undesirable conducted line frequencies in order meet electromagnetic compatibility (EMC) regulations. A circuit breaker will be included to protect the Instrument from damage caused by certain fault conditions.

The power supply must comply with safety regulations applying to medical electrical equipment, such as IEC 60601-1 and other related national variations (e.g., UL, CSA, EN). Various signals within the power supply will be monitored by the microcomputer to ensure reliable operation of the instrument.

10. System Context

ReCell NG can be used to disaggregate cells from a patient's split-thickness skin sample and to collect these cells for reintroduction to a prepared wound bed of the patient.

Indications:
In a hospital setting:
Burns, scalds and traumatic injuries
Donor sites
Large scar revision for improvement of texture and color
In a clinic setting:
Pigmentation disorders such as Vitiligo
Epidermal defects such as acne scars, hairy nevi, and skin cancer scars
Prophylactic use for healing of acute wounds
Resurfacing by laser ablation, dermabrasion or deep chemical peels
Chronic wounds (leg ulcers/hard to heal)

Figure 16:
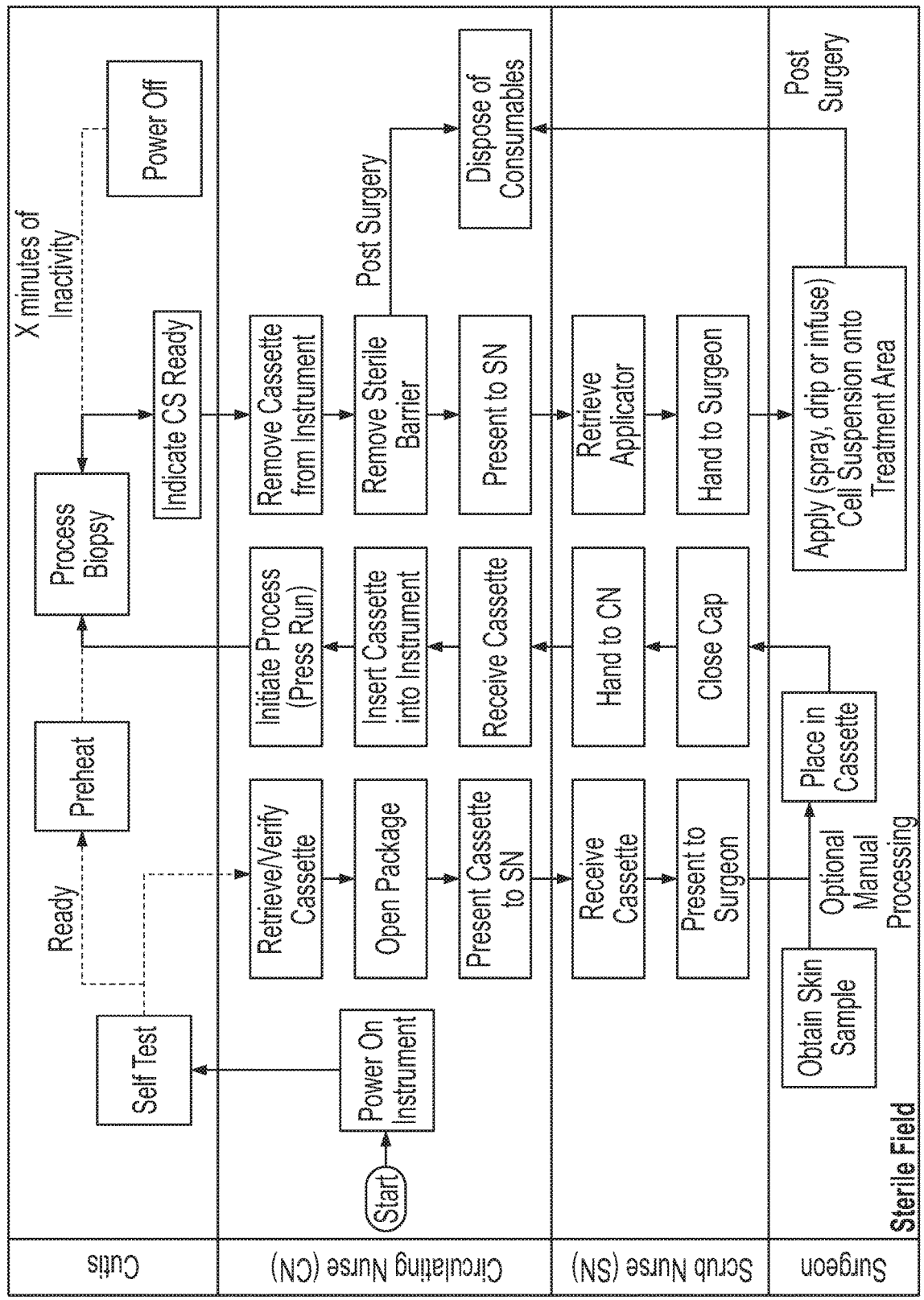
Figure 17:
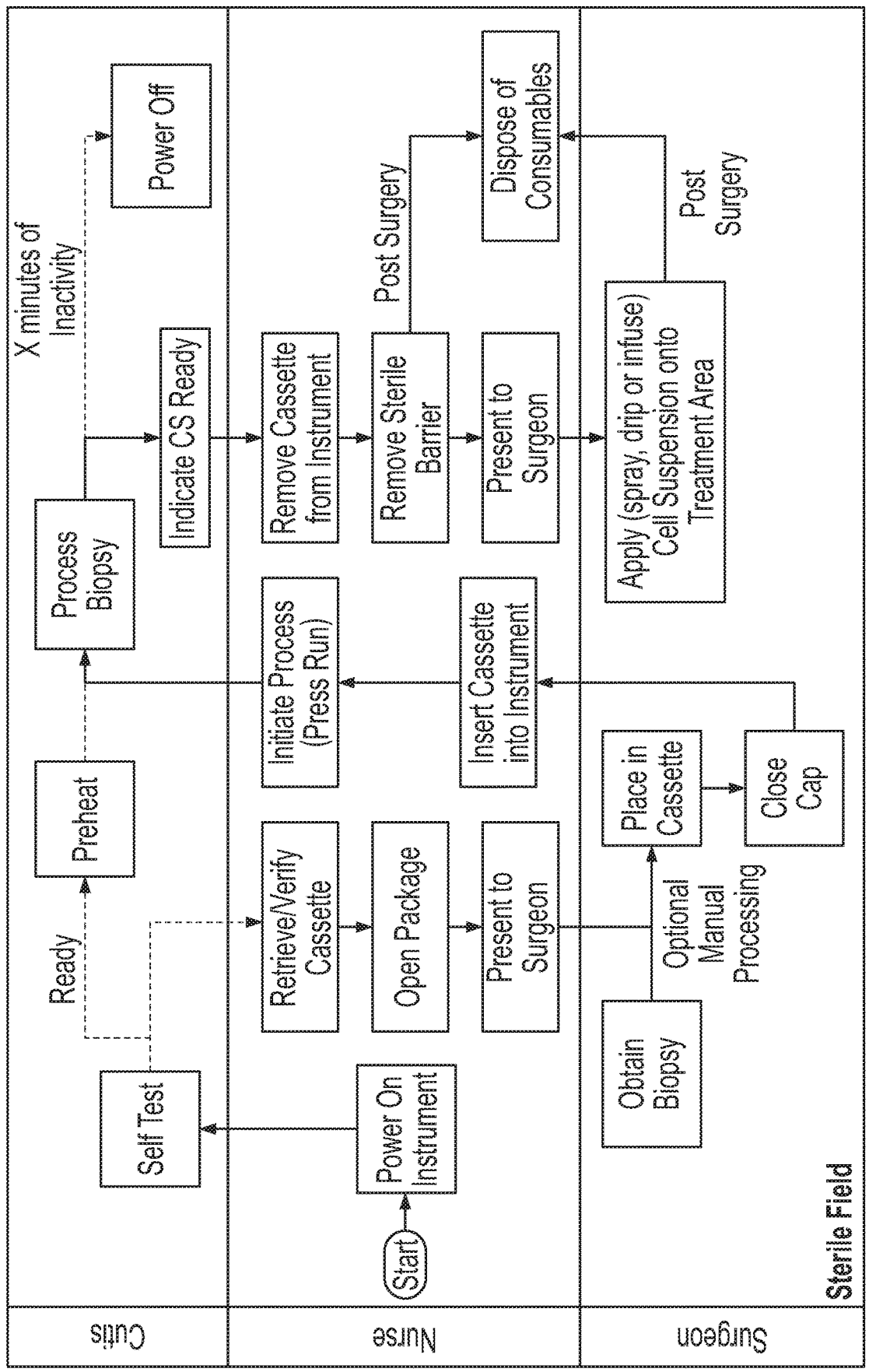
FIG. 17 illustrates a workflow for the clinic.

Two instruments can be designed:
Clinic Console:
Capable of processing two or more samples in parallel, one skin sample using one consumable
Shall accept only the small (e.g., 4 ml) cartridge and thus will be limited to a small amount (e.g., 4 ml) of cell suspension (CS)
Operating room (OR) Console:
Capable of processing two or more samples in parallel, one skin sample using one consumable
Capable of producing up to 16 ml of CS
Shall accept either small or large cartridge, but the small cartridge will be limited to a small amount (e.g., 4 ml) of CS Two consumable cartridges can be designed:
The small (e.g., 4 ml) cartridge is intended for the clinic and shall deliver up to 4 ml of cell suspension
The large (e.g., 16 ml) cartridge is intended for the OR and shall deliver up to 16 ml of cell suspension 11. Exemplary Workflow Analysis There are two separate workflows: one for the OR (FIG. 16) and one for the clinic (FIG. 17). Briefly, the workflow can include the following steps:
Load skin sample (unprocessed or partially processed (e.g., incubated in enzyme solution)) into cartridge
Insert cartridge into instrument
Set suspension volume, processing level required
Press start Cell suspension delivered to applicator in 20 minutes (with standard process) without further operator action ReCell NG Operating Room Procedure In one proposed scenario (FIG. 16), the ReCell NG Console resides in the operating room (OR), on a table, bench top, or cart, outside the sterile field. The Console is turned on to warm up and self-test. The Cassette, still in its sterile packaging (radiation sterilized during manufacturing) may also be pre-heated.

Using aseptic technique, the Cassette is introduced into the sterile field. A scrubbed-in nurse or technician opens the disaggregation chamber by removing the cap and places the tissue sample (just obtained from the patient) into the well and then replaces the cap. The cap remains, maintaining a seal throughout the process and disposal. The tissue sample is not oriented in any particular way.

The scrub nurse passes the Cassette to the circulating nurse who carries the Cassette back to the Console and inserts the Cassette into the slot on the Console, until it is seated in the console, drawn into the console or otherwise locks into place. The circulating nurse uses the Console operator interface to indicate the processing time and suspension volume needed and activates the process cycle.

The system automatically, without further input from the operator, reconstitutes the enzyme (enzyme may not be necessary if the skin sample has been partially processed before being placed in the Cassette, e.g., if the skin sample has been incubated in an enzyme solution), processes the tissue, creates and filters the suspension and loads the Applicator. During cell processing a progress display is updating and showing the status of the processing and the time remaining until processing is complete When the processing cycle is complete (approximately 30 minutes) a notification tone and light notify the user that the cell suspension is ready and in the Applicator.

The circulating nurse then removes the Cassette from the Console, carries it to the sterile field and using aseptic technique, opens the Applicator compartment and presents the sterile Applicator to the scrub nurse or physician.

The physician then applies the cell suspension onto the treatment area.

Exemplary Process steps of ReCell NG:
Tabletop unit is set up outside sterile field.
Turn on tabletop unit. Device performs automatic self-test and start heater. If outcome of self-test is acceptable, instrument prompts for inputs, including desired suspension volume.
Introduce sterile cartridge into sterile field
Surgeon takes a skin sample (shave biopsy) which is inserted into cartridge
Circulating nurse or technician inserts cartridge into the console, sets suspension volume and presses "run".
Instrument processes the tissue (presumptive process)
Dissolve Enzyme in sterile water; dwell or agitate to mix (optional)
Enzyme solution is pumped into the mortar to immerse skin sample (optional)
Start timer when temperature of enzyme solution reaches 22° C. or above
Heat to 37° C.
After appointed time, turn off heaters and drain enzyme solution to waste.

Rinse skin sample with buffer solution; drain rinse solution to waste.

Add a small volume of buffer to collect cells, process skin sample to remove and collect cells Filter cells and generate the appropriate volume of suspension for treatment area size.

Transfer suspension into delivery apparatus.

Signal complete

Cartridge removed from console and a circulating nurse or technician opens applicator compartment. Surgical nurse removes the delivery vessel, (the exterior surfaces of which remain sterile) from the still-sterile interior of the cartridge and hands to surgeon.

Surgeon sprays drips or infuses suspension onto treatment area.

12. Data

The system, internally or externally, can include a data storage unit, sufficient to maintain operational logs. For example, the Console can contain provision for logging activity for reporting, troubleshooting and continual improvement. The Console can also be provided with ability to record self-test, ready mode, input parameters, time of cartridge insertion, time of start events, and temperature/time data for at least four procedures of maximum output size for console. In addition, time-stamped data with resolution of e.g., one-second, as well as means of accessing or displaying Log can also be included.

13. Processing Parameters (Cell Suspension)

Various skin or other epithelial tissue can be obtained for processing. The tissue sample can have maximum dimensions that fits into the tissue processing chamber (e.g., about 4 cm×4 cm), and can be as small as desirable (e.g., 1.0 cm$^2$). Recommended thickness range is about 0.006-0.008" (0.15-0.20 mm) and can be thinner or thicker (e.g., 0.1" (2.54 mm)). The following is several exemplary sizes suitable to be processed by the system of the present invention:

Standard time: up to 4 cm$^2$, 0.006-0.008" thick
Medium time: up to 16 cm$^2$, 0.010-0.012" thick
Long time: up to 16 cm$^2$, up to 0.10" thick The sample is likely to be irregularly shaped, not rectangular and may potentially be thicker.

Exemplary Fluid delivery:

Reconstituting Enzyme: 10±0.2 ml (e.g., avoiding foaming, recovery of enzyme solution from container, etc.)

Rinsing skin sample with buffer after digestion: 10±1.0 ml (removing and deactivating Enzyme from skin sample)

Creating cell suspension: Volume selected by user, per Table 1, Tolerance ±0.2 ml.

Recommended skin sample sizes and the volume of buffer to be used to start is shown in Table 1.

TABLE 1

| Cell Suspension Volume Desired (CSV) | Biopsy area [BA] (cm$^2$) | Buffer used to make suspension |
|---|---|---|
| 1.0 | 1 | 1.5 |
| 1.5 | 2 | 2.0 |
| 2.0 | 4 | 2.5 |
| 2.5 | 4 | 3.0 |
| 3.0 | 4 | 3.5 |
| 3.5 | 4 | 4.0 |
| 4.0 | 4 | 4.5 |
| 5.0 | 9 | 5.5 |
| 6.0 | 9 | 6.5 |
| 7.0 | 9 | 7.5 |
| 8.0 | 9 | 8.5 |
| 9.0 | 16 | 9.5 |
| 10.0 | 16 | 10.5 |
| 11.0 | 16 | 11.5 |
| 12.0 | 16 | 12.5 |
| 13.0 | 16 | 13.5 |
| 14.0 | 16 | 14.5 |
| 15.0 | 16 | 15.5 |
| 16.0 | 16 | 16.5 |

During incubation, device can maintain temperature at a minimum of 35° C. and a maximum of 42° C. (Ambient temperature in burn operating rooms may be as high as 42° C.) After incubation, elevated temperature not required and chamber may be allowed to move to ambient temperature. (Note that since OR temperature for burn procedures is often greater than 37° C., ambient may be greater than 37° C. There is no requirement for cooling below ambient.)

Process timing: entire process can be complete in 20 minutes for standard process. Time may vary depending on the size and thickness of the sample.

The resulting cell suspension (CS) includes various viable and functioning skin cells, including differentiated, differentiating and undifferentiated cells. Some cells are capable of dividing. Some are capable of providing normal functions. Keratinocytes, Langerhans cells, fibroblasts and melanocytes can be included. In some embodiments, 4 ml of CS can be used for maximum treatment areas up to 320 cm$^2$ and 16 ml of CS for maximum treatment areas up to 1280 cm$^2$.

The output of cell disaggregation process can be filtered using a 100 μm or other size filter to remove larger particles. The resulting cell suspension (CS) fluid is transferred to Applicator. The volume of the output can be set by the operator.

Waste from the process shall be contained within the consumable for disposal in line with guidance and practice for biologic materials for the region of use. Both expended cartridge and used applicator, or any components therein can be treated as biologic waste.

14. Environmental Requirements

The ReCell NG System shall operate according to its defined specifications under the following operating conditions:

| | |
|---|---|
| Temperature: | 10° C.-42° C. |
| Relative Humidity: | 5%-95%, non-condensing |
| Atmospheric Pressure: | From 1500 ft below sea level to 6500 ft above sea level (15.51 psiA-11.56 psiA or 106.9 kPa-79.7 kPa) |

The ReCell NG System shall operate according to its defined specifications after being exposed to the following transport conditions:

| | | |
|---|---|---|
| Temperature | Console: | −20° C.-60° C. |
| | Cartridges: | −4° C.-30° C. |
| Relative Humidity: | | up to 95%, non-condensing |
| Atmospheric Pressure: | | From 1500 ft below sea level to 19000 ft above sea level (15.51 psiA-7.04 psiA or 106.9 kPa-48.5 kPa) |

The ReCell NG System shall operate according to its defined specifications after being exposed to the following storage conditions:

| | | |
|---|---|---|
| Temperature | Console: | −20° C.-60° C. |
| | Cartridges: | 2° C.-30° C. |
| Relative Humidity: | | up to 95%, non-condensing |
| Atmospheric Pressure: | | From 1500 ft below sea level to 19000 ft above sea level (15.51 psiA-7.04 psiA or 106.9 kPa-48.5 kPa) |

The ReCell NG System shall operate according to its defined specifications after being exposed to the ASTM D 4728 Standard Test Method for Random Vibration Testing of Shipping Containers.

Modifications and variations of the described methods and device of the invention will be apparent to those skilled in the art without departing from the scope and spirit of the invention. Although the invention has been described in connection with specific preferred embodiments, it should be understood that the invention as claimed should not be unduly limited to such specific embodiments. Indeed, various modifications of the described modes for carrying out the invention which are obvious to those skilled in the relevant field in which this invention resides are intended to be within the scope of the claims.

The invention claimed is:

1. A system for cell harvesting and transplant, comprising:
a cartridge for processing a tissue, the cartridge comprising a tissue processing chamber, a disintegrator situated therein on which the tissue sits, a cap coupled to the tissue processing chamber, and a cell collection chamber separated from the tissue processing chamber by the disintegrator; and
a programmable console for removably housing the cartridge, wherein the console comprises a disintegrating member, an actuating mechanism, and a processor for controlling the actuating mechanism such that the disintegrating member exerts compression and a rotational force on the tissue through the cap without the disintegrating member contacting the tissue, thereby mechanically dissociating the tissue,
wherein after dissociating the tissue and passing the dissociated tissue through the disintegrator, a cell suspension is collected in the cell collection chamber.

2. The system of claim 1, wherein the cartridge further comprises a container for providing a solution comprising a chemical reagent, wherein the chemical reagent is capable of breaking down extracellular matrix in the tissue.

3. The system of claim 2, wherein the console further comprises a pressurizing mechanism for driving the solution out of the container and into the tissue processing chamber, thereby chemically dissociating the tissue therein.

4. The system of claim 1, wherein the cartridge further comprises a first packet for providing an enzyme solution and a second packet for providing a buffer solution, both packets in fluid communication with the tissue processing chamber, wherein the enzyme solution breaks down extracellular matrix in the tissue thereby chemically dissociating the tissue, and wherein the buffer solution washes the dissociated tissue and suspends cells in the cell suspension.

5. The system of claim 4, wherein the first packet has a first and a second container separated by a breakable seal, the first container containing sterile water and the second container containing lyophilized enzyme powder, wherein when the seal is broken, the lyophilized enzyme powder meets the sterile water and dissolves therein.

6. The system of claim 1, wherein the cap is removably placed on or hinged to the tissue processing chamber and comprises a seal including a flexible portion for sealing the tissue processing chamber.

7. The system of claim 6, wherein the seal has a first side and a second side, wherein the first side faces the tissue processing chamber and has a working surface, wherein the second side faces the disintegrating member, and wherein when the disintegrating member is actuated and placed upon the second side, the working surface is in contact with the tissue placed in the tissue processing chamber such that the compression and the rotational force is applied through the seal.

8. The system of claim 1, wherein the cartridge further comprises at least one supplying container for providing an exogenous agent.

9. The system of claim 8, wherein the exogenous agent is a heat shock protein or a fragment thereof, hyaluronic acid, platelet-enriched plasma, a growth factor, adipose stem cells, or any combination of the foregoing.

10. The system of claim 1, wherein the disintegrating member is a reciprocating-rotating member, and the disintegrator is a mesh, screen, grid, blade, or any combination thereof.

11. The system of claim 1, wherein the cartridge further comprises another disintegrating member situated in the tissue processing chamber.

12. The system of claim 1, wherein the cartridge further comprises a mechanism for balancing pressure during fluid movement, wherein preferably the mechanism is an antimicrobial filter or a bore tortuous path.

13. The system of claim 1, wherein a disposable applicator is removably in fluid communication, directly or indirectly, with the cell collection chamber and capable of receiving the cell suspension therefrom.

14. The system of claim 13, wherein the disposable applicator is capable of dispensing, spraying or dripping the cell suspension therein onto a recipient site or a scaffold.

15. The system of claim 13, wherein an outer surface of the disposable applicator is sealed in a sterile packaging before transport to a sterile field for cell transplant.

16. The system of claim 1, further comprising a custom control software for directing the processor.

17. The system of claim 1, being connected to an external computer for collecting and processing data.

18. The system of claim 1, wherein the cartridge further comprises a mechanism for providing motive power to supply a mechanical force and/or a chemical reagent to the tissue.

19. The system of claim 1, further comprising a support for receiving the cell suspension, wherein the support, after receiving the cell suspension, is presented for transplant or culturing.

20. The system of claim 19, wherein the support is a matrix, a scaffold, a dressing, or any combination thereof.

21. The system of claim 19, wherein the support is solid, semi-solid, porous or fragmented.

22. A method of cell harvesting and transplant using the system of claim 1, comprising:
placing the tissue in the tissue processing chamber;
directing the console to actuate the disintegrating member; and
retrieving a disposable applicator having the cell suspension therein.

23. A method of cell harvesting and transplant using the system of claim 1, comprising:
   placing the tissue in the tissue processing chamber;
   directing the processor in the console so as to supply a mechanical force and/or chemical reagent to the tissue; and
   retrieving the cell suspension.

24. The system of claim 1, wherein the cartridge further comprises a filter situated between the disintegrator and the cell collection chamber, for filtering the processed tissue to remove large aggregates.

25. The system of claim 1, wherein the cartridge further comprises a filter situated downstream from the cell collection chamber, for filtering the cell suspension to remove large aggregates.

* * * * *